(12) United States Patent
Newman

(10) Patent No.: US 10,052,371 B2
(45) Date of Patent: *Aug. 21, 2018

(54) COMPOSITIONS AND METHODS FOR TREATMENT OF CANCER USING BACTERIA

(71) Applicant: Decoy Biosystems, Inc., San Diego, CA (US)

(72) Inventor: Michael J. Newman, San Diego, CA (US)

(73) Assignee: Decoy Biosystems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/003,726

(22) Filed: Jan. 21, 2016

(65) Prior Publication Data

US 2016/0199422 A1 Jul. 14, 2016

Related U.S. Application Data

(63) Continuation of application No. 14/139,063, filed on Dec. 23, 2013, now Pat. No. 9,265,804.

(60) Provisional application No. 61/748,369, filed on Jan. 2, 2013.

(51) Int. Cl.
| | |
|---|---|
| A61K 35/74 | (2015.01) |
| A61K 45/06 | (2006.01) |
| C12N 1/36 | (2006.01) |
| A61K 31/664 | (2006.01) |
| A61K 39/00 | (2006.01) |
| C12N 1/20 | (2006.01) |

(52) U.S. Cl.
CPC ........ *A61K 39/0011* (2013.01); *A61K 31/664* (2013.01); *A61K 35/74* (2013.01); *A61K 45/06* (2013.01); *C12N 1/20* (2013.01); *C12N 1/36* (2013.01); *A61K 2039/522* (2013.01); *A61K 2039/523* (2013.01); *A61K 2039/585* (2013.01); *Y02A 50/473* (2018.01); *Y02A 50/481* (2018.01)

(58) Field of Classification Search
CPC ........ A61K 2039/522; A61K 2039/523; A61K 2039/585; A61K 31/664; A61K 35/74; A61K 39/0011; A61K 45/06; C12N 21/20; C12N 1/36; Y02A 50/481
See application file for complete search history.

(56) References Cited

U.S. PATENT DOCUMENTS

| | | | |
|---|---|---|---|
| 4,436,727 A | 3/1984 | Ribi | |
| 4,842,855 A | 6/1989 | Youngner et al. | |
| 5,171,738 A | 12/1992 | Kodama et al. | |
| 5,510,242 A | 4/1996 | Blais et al. | |
| 5,811,097 A | 9/1998 | Allison et al. | |
| 6,190,657 B1 | 2/2001 | Pawelek et al. | |
| 6,264,952 B1 | 7/2001 | Enright et al. | |
| 6,548,287 B1 | 4/2003 | Powell et al. | |
| 6,685,935 B1 | 2/2004 | Pawelek et al. | |
| 7,344,710 B2 | 3/2008 | Dang et al. | |
| 7,354,592 B2 | 4/2008 | Bermudes et al. | |
| 7,452,531 B2 | 11/2008 | Bermudes et al. | |
| 8,007,782 B2 | 8/2011 | Dang et al. | |
| 8,034,359 B2 | 10/2011 | Gunn | |
| 9,265,804 B2 * | 2/2016 | Newman | A61K 35/74 |
| 2004/0166102 A1 | 8/2004 | Darouiche et al. | |
| 2004/0229338 A1 | 11/2004 | King | |
| 2009/0074816 A1 | 3/2009 | Gunn | |
| 2009/0300779 A1 | 12/2009 | Zhao et al. | |
| 2010/0272758 A1 | 10/2010 | Woodard et al. | |
| 2011/0020401 A1 * | 1/2011 | Gunn | A61K 39/0011 424/234.1 |
| 2011/0224097 A1 | 9/2011 | Bramhill et al. | |
| 2016/0228523 A1 | 8/2016 | Newman | |

FOREIGN PATENT DOCUMENTS

| | | |
|---|---|---|
| EP | 1765391 | 3/2013 |
| WO | WO 1996/030043 | 10/1996 |
| WO | WO-1998/053851 | 12/1998 |
| WO | WO-2001/024637 | 4/2001 |
| WO | WO-2003/063593 | 8/2003 |
| WO | WO-2005/120560 | 12/2005 |
| WO | WO 2007/084633 | 7/2007 |

OTHER PUBLICATIONS

Belunis et al. J. Biol. Chem. 267: 9988-9997, 1992.*
Ronneberger HJ. Dev. Biol. Stand. 34: 27-36, 1977, abstract.*
Kochman M. Biopharm International Aug. 31, 2006.*
Fransen et al., "Naturally occurring lipid a mutants in Neisseria meningitidis from patients with invasive meningococcal disease are associated with reduced coagulopathy", PLoS Pathogens, vol. 5, Issue 4, pp. 1-12, Apr. 2009.

(Continued)

*Primary Examiner* — Sarvamangala Devi
(74) *Attorney, Agent, or Firm* — Sheppard Mullin Richter & Hampton LLP

(57) ABSTRACT

Provided herein are compositions comprising substantially non-viable Gram-negative bacterial organisms that have a substantial reduction in endotoxin activity and/or pyrogenicity and methods for treating a cancer using the same. Also provided are methods for treating cancer provided herein, comprising administering to a mammal diagnosed with cancer, substantially non-viable Gram-negative bacteria having a substantial reduction in endotoxin activity and/or pyrogenicity, in an amount sufficient to inhibit growth or metastasis of the cancer. An additional method is provided comprising administering viable or non-viable Gram-negative bacterial organisms that have a genetic defect that results in a substantial loss of lipopolysaccharide within the outer membrane of the bacteria. Further provided are methods for reducing endotoxin activity and/or pyrogenicity in Gram-negative bacteria comprising treatment with polymyxin and glutaraldehyde.

12 Claims, 6 Drawing Sheets

(56) References Cited

OTHER PUBLICATIONS

Moffatt et al., "Colistin resistance in Acinetobacter baumannii is mediated by complete loss of lipopolysaccharide production", Antimicrobial Agents and Chemotherapy, vol. 54, No. 12, pp. 4971-4977, Dec. 2010.
American Type Culture Collection Bacterial Culture Guide, 2012, 35 pages.
Appleyard et al., "Phenformin as prophylaxis and therapy in breast cancer xenografts", Brit. J. Cancer, 2012, vol. 106, pp. 1117-1122.
Belunis et al., "Inhibition of Lipopolysaccharide Biosynthesis and Cell Growth Following Inactivation of the kdtA Gene in *Escherichia coli,*" *The Journal of Biological Chemistry*, vol. 270, No. 46, Nov. 17, 1995, pp. 27646-27652.
Brahmer Jr., et al., "Phase I study of single-agent anti-programmed death-1 (MDX-1106) in refractory solid tumors: safety, clinical activity, pharmacodynamics, and immunologic correlates", J. Clin. Oncol., 2010, vol. 28, pp. 3167-3175.
Brahmer Jr., et al., "Safety and activity of anti-PD-L1 antibody in patients with advanced cancer", N. Engl. J. Med., 2012, vol. 366, pp. 2455-2465.
Bukhari et al., Genetic Analysis of Diaminopimelic Acid- and Lysine-Requiring Mutants of *Escherichia coli, J. Bacteriol.*, vol. 105 No. 3, Mar. 1971, pp. 844-854.
Cooperstock et al., "Polymyxin B Inactivation of Lipopolysaccharide in Vaccines of Gram-Negative Bacteria," *Infection and Immunity*, vol. 33, No. 1, Jul. 1981, pp. 315-318.
Curtiss et al., Recombinant Avirulent *Salmonella* Vaccine Strains with Stable Maintenance and High Level Expression of Cloned Genes in vivo, *Immunol. Invest.*, vol. 18 No. 1-4, May 1989, pp. 583-596.
Daugelavicius et al., "Stages of Polymyxin B Interaction with the *Escherichia coli* Cell Envelope", Antimicrobial Agents and Chemotherapy, Nov. 2000, vol. 44, No. 11, pp. 2969-2978.
Del Barco et al., "Metformin: multi-faceted protection against cancer", Oncotarget, 2011, vol. 2(12), pp. 896-917.
Deng et al., "Metformin targets Stat3 to inhibit cell growth and induce apoptosis in triple-negative breast cancers", Cell Cycle, 2012, vol. 11(2), pp. 367-376.
Eisenhauer et al., "New response evaluation criteria in solid tumours: revised RECIST guideline (version 1.1)", Eur. J. Cancer, 2009, vol. 45(2), pp. 228-247.
Eisenstein et al., "Immunotherapy of a Plasmacytoma with Attenuated *Salmonella,*" *Medical Oncology*, vol. 12, No. 2, Jun. 1995, pp. 103-108.
Feingold et al., "Antiviral Activity of *Brucella abortus* Preparations: Separation of Active Components", Infection and Immunity, Mar. 1976, vol. 13, No. 3, pp. 763-767.
Freeman et al., "Engagement of the PD-1 immunoinhibitory receptor by a novel B7 family member leads to negative regulation of lymphocyte activation", J. Exp. Med., 2000, vol. 192(7), pp. 1027-1034.
Garber et al., "Beyond ipilimumab: new approaches target the immunological synapse", J. Natl. Cancer Inst., 2011, vol. 103(14), pp. 1079-1082.
Goldman et al., "Analysis of Lipopolysaccharide Biosynthesis in *Salmonella typhimurium* and *Escherichia coli* by Using Agents Which Specifically Block Incorporation of 3-Deoxy-D-manno-Octulosonate," *Journal of Bacteriology*, May 1988, vol. 170, pp. 2185-2191.
Gu et al., "Some observations in freeze-drying of recombinant bioluminescent *Escherichia coli* for toxicity monitoring", J. Biotech., 2001, vol. 88, pp. 95-105.
Gupta et al., "Immunogenicity of Glutaraldehyde Inactivated Pertussis Vaccine," *Vaccine*, vol. 8, Dec. 1990, pp. 563-568.
Havas et al., "Clinical Results and Immunologic Effects of a Mixed Bacterial Vaccine in Cancer Patients," *Med. Oncol. & Tumour Pharmacother.*, vol. 10, No. 4, 1993, pp. 145-158.
Hirsch et al., "Metformin inhibits the inflammatory response associated with cellular transformation and cancer stem cell growth", PNAS, 2013, vol. 110, No. 3, pp. 972-977.
Hoffman, "Tumor-targeting amino acid auxotrophic *Salmonella typhimurium*", Amino Acids, 2009, vol. 37, No. 3, pp. 509-521.
International Searching Authority, "Invitation to Pay Additional Fees and, Where Applicable, Protest Fee," dated Mar. 13, 2014, 8 pages.
International Search Report and Written Opinion for PCT/US2012/045086 dated Sep. 19, 2012, 12 pages.
International Search Report and Written Opinion for PCT/US2013/077441 dated Jun. 2, 2014, 18 pages.
Ishida et al., "Induced expression of PD-1, a novel member of the immunoglobulin gene superfamily, upon programmed cell death", EMBO. J., 1992, vol. 11, pp. 3887-3895.
Jia et al., "Tumor-Targeting *Salmonella typhimurium* Improves Cyclophosphamide Chemotherapy at Maximum Tolerated Dose and Low-Dose Metronomic Regimens in a Murine Melanoma Model", *Int. J. Cancer*, vol. 121 No. 3, Aug. 1, 2007, pp. 666-674.
Jiralerspong et al., "Metformin and pathologic complete responses to neoadjuvant chemotherapy in diabetic patients with breast cancer", J. Clin. Oncol., 2009, vol. 27(20), pp. 3297-3302.
Jones "Bacterial Endotoxins and Pyrogens", Int. J. Pharm. Compd., 2001, vol. 5(4), pp. 259-263.
Khong et al., "The use of agonistic anti-CD40 therapy in treatments for cancer", Int. Rev. Immunol., 2012, vol. 31(4), pp. 246-266.
Kim-Schulze et al., "Cytokine Therapy for Cancer", Surg. Onc. Clinics N. Amer., 2007, vol. 16(4), pp. 793-818.
Latchman et al., "PD-L2 is a second ligand for PD-1 and inhibits T cell activation", Nat. Immunol., 2001, vol. 2(3), pp. 261-318.
Leslie et al., "Trehalose and sucrose protect both membranes and proteins in intact bacteria during drying" App. Environment Microbiol., 1995, vol. 61(10), pp. 3592-3597.
Lipson et al., "Durable Cancer Regression Off-Treatment and Effective Reinduction Therapy with an Anti-PD-1 Antibody", Clin. Can. Res., 2013, vol. 19, pp. 462-468.
Lockyer et al., "BCG Immunotherapy for Superficial Bladder Cancer", Journal of the Royal Society of Medicine, vol. 94, Mar. 2001, pp. 119-123.
Low et al., "Lipid A Mutant *Salmonella* with Suppressed Virulence and TNFα Induction Retain Tumor-Targeting in Vivo," *Nature Biotechnology*, vol. 17, Jan. 1999, pp. 37-41.
Luo et al., "Antitumor Effect of VNP20009, An Attenuated *Salmonella*, in Murine Tumor Models," *Oncological Research*, vol. 12, Nos. 11-12, 2001, pp. 501-508.
Maletzki et al., "Bacteriolytic Therapy of Experimental Pancreatic Carcinoma," *World Journal of Gastroenterology*, vol. 16, No. 28, Jul. 2010, pp. 3546-3552.
Maletzki et al., "Reevaluating the Concept of Treating Experimental Tumors with a Mixed Bacterial Vaccine: Coley's Toxin," *Clinical and Developmental Immunology*, vol. 2012, Article ID 230625, 2012, 16 pages.
Mamat et al., "Single Amino Acid Substitutions in Either YhjD or MsbA confer Viability to 3-Deoxy-D-Manno-Oct-2-Ulosonic Acid-Depleted *Escherichia coli,*" *Molecular Microbiology*, vol. 67, No. 3, 2008, pp. 633-648.
Melero et al., "Palettes of vaccines and immunostimulatory monoclonal antibodies for combination", Clin. Cancer Res., 2009, vol. 15(5), pp. 1507-1509.
Park et al., "Targeting and blocking B7 costimulatory molecules on antigen-presenting cells using CTLA4Ig-conjugated liposomes: in vitro characterization and in vivo factors affecting biodistribution", Pharm. Res., 2003, vol. 20(8), pp. 1239-1248.
Pawelek et al., "Bacteria as Tumour-Targeting Vectors," *The Lancet Oncology*, vol. 4, Sep. 2003, pp. 548-556.
Rebe et al., "STAT3 activation: A key factor in tumor immunoescape", JAK-STAT, 2013, vol. 2(1), p. e23010.
Relyveld et al., "Preparation of Vaccines by the Action of Glutaraldehyde on Toxins, Bacteria, Viruses, Allergens and Cells," *Methods in Enzymology*, vol. 93, 1983, pp. 24-60.
Rick et al., "Isolation of a Mutant of *Salmonella typhimurium* Dependent on D-Arabinose-5-Phosphate for Growth and Synthesis

(56) References Cited

OTHER PUBLICATIONS of 3-Deoxy-D-Mannoctulosonate (Ketodeoxyoctonate)," *Proc. National Academy of Science*, vol. 69, No. 12, Dec. 1972, pp. 3756-3760.
Rutala et al., "New Disinfection and Sterilization Methods," *Emerging Infectious Diseases*, vol. 7, No. 2, Mar.-Apr. 2001, pp. 348-353.
Ryoma et al., "Biological Effect of OK-432 (Picibanil) and Possible Application to Dendritic Cell Therapy," *Anticancer Research*, vol. 24, 2004, pp. 3295-3302.
Schafer et al., "Induction of Activated Macrophages in C3H/HeJ Mice by Avirulent *Salmonella*," *Journal of Immunology*, vol. 140, No. 5, Mar. 1, 1988, pp. 1638-1644.
Shintani "Validation of sterilization procedures and usage of biological indicators in the manufacture of healthcare products", Biocontrol Science, 2011, vol. 16(3), pp. 85-94.
Smyth et al., "Cytokines in cancer immunity and immunotherapy", Imm. Rev., 2004, vol. 202, pp. 275-293.
Snell "T-cell intrinsic effects of GITR and 4-1 BB during viral infection and cancer immunotherapy", Immunol. Rev., 2011, vol. 244(1), pp. 197-217.
So et al., "Immune regulation and control of regulatory T cells by OX40 and 4-1 BB", Cytokine Growth Factor Rev., 2008, vol. 19(3-4), pp. 253-262.
Taylor et al., "A Single Point Mutation in 3-deoxy-D-mannooctulosonate-8-phosphate synthase is Responsible for Temperature Sensitivity in a Mutant strain of *Salmonella typhimurium*", *J. Biol. Chem.* Oct. 13, 2000, vol. 275 No. 41, pp. 32141-32146.
Therasse et al., "New guidelines to evaluate the response to treatment in solid tumors. European Organization for Research and Treatment of Cancer, National Cancer Institute of the United States, National Cancer Institute of Canada", J. Natl. Cancer Inst., 2000, vol. 92, pp. 205-216.
Toso et al., "Phase I Study of the Intravenous Administration of Attenuated *Salmonella typhimurium* to Patients with Metastatic Melanoma," *Journal of Clinical Oncology*, vol. 20, No. 1, Jan. 1, 2002, pp. 142-152.
U.S. Pharmacopeia, Chapter 151, Pyrogen Test, 2005, p. 2546.
Van Amersfoort et al., "Receptors, Mediators, and Mechanisms Involved in Bacterial Sepsis and Septic Shock", Clinical Microbiology Reviews, Jul. 2003, vol. 16, No. 3, pp. 379-414.
Vinay et al., "Immunotherapy of cancer with 4-1 BB," *Mol. Cancer Ther.*, 2012, vol. 11, No. 5, pp. 1062-1070.

Wiemann et al., "Coley's Toxins, Tumor Necrosis Factor and Cancer Research: A Historical Perspective," *Pharmac. Ther.*, vol. 64, 1994, pp. 529-564.
Yaman "Alternative Methods of Terminal Sterilization for Biologically Active Macromolecules", *Curr. Opins Drug Discovs Devel.*, vol. 4, No. 6, Nov. 2001, pp. 760-763.
Youngner et al., "Antiviral Activity of an Ether-Extracted Nonviable Preparation of *Brucella abortus*," Infect Immun. Dec. 1974;10(6):1202-6.
Zhao et al., "Tumor-Targeting Bacterial Therapy With Amino Acid Auxotrophs of GFP-Expressing *Salmonella typhimurium*," *PNAS*, vol. 102, No. 3, Jan. 18, 2005, pp. 755-760.
Zu et al., "Tumor-Colonizing Bacteria: A Potential Tumor Targeting Therapy," *Critical Review in Microbiology*, vol. 40, No. 3, 2014, pp. 225-235.
Alipour, et al. Antimicrobial effectiveness of liposomal polymyxin B against resistant Gram-negative bacterial strains. Int J Pharm. May 1, 2008;355(1-2):293-8. doi: 10.1016/j.ijpharm.2007.11.035. Epub Nov. 24, 2007.
He, et al. Stability of polymyxin B sulfate diluted in 0.9% sodium chloride injection and stored at 4 or 25 degrees C. Am J Health Syst Pharm. Jul. 15, 2010;67(14):1191-4. doi: 10.2146/ajhp090472.
Munton et al., "Effect of Glutaraldehyde on the Outer Layers of *Escherichia coli*", J. appl. Bact., vol. 35, p. 193-199, 1972.
Murray et al., "Extragenic Suppressors of Growth Defects in msbB *Salmonella*", Journal of Bacteriology, Oct. 2001, vol. 183, No. 19, p. 5554-5561.
Stokes et al., "Polymyxin B Prevents Lipopolysaccharide-Induced Release of Tumor Necrosis Factor-a from Alveolar Macrophages", The Journal of Infectious Diseases, vol. 160, p. 52-57, 1989.
Stritzker et al., "Myristoylation Negative msbB-mutants of Probiotic *E. coli* Nissle 1917 Retain Tumor Specific Colonization Properties but Show Less Side Effects in Immunocompetent Mice", Bioengineered Bugs, 1:2, p. 139-145, 2010.
Suganuma et al., "Cytological Changes of *Escherichia Coli* Caused by Polymyxin E", Bikin Journal, vol. 11, p. 149-155, 1968.
Wang, "Safety Issues of Metalworking Fluids", Synthetic Lubricants, 2003, p. 30-33 (English abstract).
Westendorf et al., "Intestinal immunity of *Escherichia coli* NISSLE 1917: a Safe Carrier for Therapeutic Molecules", FEMS Immunology and Medical Microbiology, vol. 43, p. 373-384, 2005.

* cited by examiner

COMPOSITIONS AND METHODS FOR TREATMENT OF CANCER USING BACTERIA

CROSS REFERENCE TO RELATED APPLICATIONS

This application is a continuation of U.S. application Ser. No. 14/139,063, filed Dec. 23, 2013, now issued as U.S. Pat. No. 9,265,804, which claims the benefit under 35 U.S.C. § 119(e) to U.S. provisional application 61/748,369 filed Jan. 2, 2013, the contents of both of which are hereby incorporated by reference.

FIELD

This disclosure relates to compositions comprising Gram-negative bacteria and methods for treating cancer by administering the same.

BACKGROUND

The association of cancer regression in patients undergoing bacterial infection was observed and reported at least as early as 1868. The systemic administration of live attenuated *Salmonella* organisms to solid tumor bearing animals was reported to result in tumor therapy. See, e.g., U.S. Pat. No. 6,685,935 and Pawelek et al., (Lancet Oncol. 4(9):548-56, 2003). Also, intravesical (non-systemic) administration of attenuated Gram-positive mycobacteria (BCG) is approved in the United States for the treatment and prophylaxis of carcinoma in situ (CIS) of the urinary bladder.

Improvements in tumor therapy using live Gram-negative *Salmonella* have also been reported for certain auxotrophic mutants. See e.g., Hoffman et al., (Amino Acids 37:509-521, 2009, U.S. Patent publication 20090300779 (Zhao et al.), and Zhao et al. (Proc. Natl. Acad. Sci. (USA) 102(3):775-760, 2005).

*Salmonella* having deletions in the msbB locus have been prepared which express LPS lacking terminal myristoylation of lipid A in the outer membrane. TNF-alpha induction in mice and swine treated with these msbB-*Salmonella* strains was 33% and 14% of the amount induced by wild-type bacteria, respectively. See e.g., Low et al., Nature 17:37-41, 1999 and U.S. Pat. No. 7,354,592 (Bermudes et al.). Administration of such live organisms, including strain VNP20009, has been reported to inhibit the growth of subcutaneously implanted B16F10 murine melanoma, and the human tumor xenografts Lox, DLD-1, A549, WiDr, HTB177, and MDA-MB-231 grown in mice (Luo et al., Oncol. Res. 12(11-12): 501-508, 2001). *Salmonella* strain VNP20009 has also been reported to improve the anti-tumor efficacy of the chemotherapeutic agent cyclophosphamide at both a maximum tolerated dose and with a low-dose metronomic regimen (Jia et al., Int. J. Cancer 121(3):666-674, 2007).

Conditional mutants of Gram-negative bacteria that cannot produce Lipid A and that lack LPS in the outer membrane have been prepared but have been reported to be toxic to the organism. For example, mutational inhibition of synthesis of 3-deoxy-D-manno-octulosonate (Kdo) or mutational inhibition of incorporation of Kdo molecules into lipid $IV_A$ prevents lipid A and LPS synthesis and localization of LPS precursors to the outer membrane of Gram-negative bacteria. Lipid $IV_A$ is an LPS precursor that lacks glycosylation. Activation of these mutations leads to loss of bacterial viability (Rick et al., Proc. Natl. Acad. Sci. USA 69(12): 3756-3760, 1972, Belunis et al. J. Biol. Chem. 270(46): 27646-27652, 1995, and Taylor et al. J. Biol. Chem. 275 (41):32141-32146, 2000).

It is also possible to inhibit Kdo incorporation into lipid $IV_A$, synthesis of lipid A and localization to the outer membrane through the use of exogenously added compounds. Goldman et al. (J Bacteriol. 170(5):2185-91, 1988) describe antibacterial agents that specifically inhibit CTP: CMP-3-deoxy-D-manno-octulosonate cytidylyltransferase activity, thereby blocking the incorporation of 2-keto 3-deoxy-D-manno-octulosonate (Kdo) into lipid $IV_A$ of Gram-negative organisms. As LPS synthesis ceased, molecules similar in structure to lipid $IV_A$ were found to accumulate, and bacterial growth ceased. The authors concluded that addition of Kdo to LPS precursor lipid species $IV_A$ is the major pathway of lipid A-$Kdo_2$ formation in both *S. typhimurium* LT2 and *Escherichia coli* (*E. coli*).

More recently, mutants of Gram-negative bacteria have been prepared that lack LPS, including lipid A or 6-acyl lipidpolysaccharide, in the outer membrane but maintain viability. For example, U.S. Patent publication 2010/0272758 reports an *E. coli* K-12 strain KPM22 that is defective in synthesis of 3-deoxy-d-manno-oct-2-ulosonic acid (Kdo). KPM22 has an outer membrane (OM) composed predominantly of lipid $IV_A$. Viability of these organisms was achieved by the presence of a second-site suppressor that facilitates transport of lipid $IV_A$ from the inner membrane to the outer membrane. This suppressor is reported to relieve toxic side-effects of lipid $IV_A$ accumulation in the inner membrane and provide sufficient amounts of LPS precursors to support OM biogenesis. The LPS precursor produced by this strain lacks endotoxin activity, as determined by its inability to induce TNF-alpha secretion by human mononuclear cells at LPS precursor doses of up to 1 µg/mL. See also, Mamat et al., (Mol Microbiol. 67(3):633-48, 2008).

Dose-limiting side effects associated with infection and septic shock significantly limit systemic administration of live bacteria to cancer patients. This limitation has been associated with wildtype bacteria (see e.g., Wiemann and Starnes, Pharmac. Ther. 64:529-564, 1994 for review), and has also been associated with genetically attenuated bacteria, which proliferate selectively in tumor tissue and express modified lipid A (see e.g., Toso et al., J. Clin. Oncol. 20(1):142-152, 2002). These limitations have led to the use of heat killed bacteria for cancer therapy. See e.g., Havas et al. (Med. Oncol. & Tumour Pharmacother. 10(4):145-158, 1993), Ryoma et al. (Anticancer Res. 24:3295-3302, 2004), Maletzki et al. (Clin. Develop. Immunol. 2012:1-16, 2012), U.S. Pat. No. 8,034,359 B2 (Gunn), European Patent No. EP 1,765,391 B1 (Gunn), and for review, Wiemann and Starnes (Pharmac. Ther. 64:529-564, 1994). However, non-infectious, killed bacteria still induce significant dose-limiting toxicities associated with LPS-derived endotoxin and other cell constituents, which are pyrogenic and can produce symptoms of septic shock. Thus, further improvements in treating cancer with bacteria are needed.

SUMMARY

Provided herein are compositions and methods for treating cancer in a mammal (e.g., a human), diagnosed as having cancer, by administering to that mammal an amount of Gram-negative bacteria wherein the bacteria are (i) non-viable or substantially non-viable in the mammal, (ii) have a substantial reduction in endotoxin activity and/or pyrogenicity, and (iii) are administered in an amount sufficient to inhibit the growth or metastatic potential of the cancer. In some embodiments, the Gram-negative bacteria are rendered non-viable or substantially non-viable prior to administration to the mammal by treatment with (i) radiation, (ii) a chemical sterilant, (iii) an antibiotic that inactivates endotoxin (e.g., polymyxin B or polymyxin E), or (iv) an antibiotic that disrupts the biosynthesis of KDO2-Lipid $IV_A$. Alternatively, or in addition to, any one or more of the foregoing treatments, the Gram-negative bacteria further comprises a genetic defect that disrupts or partially disrupts the biosynthesis of KDO2-Lipid $IV_A$ or prevents the O-acylation of KDO2-Lipid $IV_A$. Genetic defects that disrupt or partially disrupt the O-acylation of KDO2-Lipid $IV_A$ include, for example, defects which functionally disrupt the msbB and lpxM loci.

In one aspect of the disclosure, compositions comprise substantially non-viable Gram-negative bacteria having a substantial reduction in endotoxin activity and/or pyrogenicity and a pharmaceutically acceptable excipient. In one embodiment, the Gram-negative bacteria are made non-viable by treatment with glutaraldehyde. In another embodiment, the endotoxin activity and/or pyrogenicity is reduced by treatment with polymyxin B or polymyxin E. In a further embodiment, the endotoxin activity and/or pyrogenicity is reduced by treatment with glutaraldehyde.

In another aspect, methods are provided to treat a mammal diagnosed as having cancer which included administering an amount of substantially non-viable Gram-negative bacteria having a substantial reduction in endotoxin activity and/or pyrogenicity, wherein the amount administered is sufficient to inhibit growth or metastasis of the cancer.

In another aspect, the disclosure provides methods for treating cancer in a mammal (e.g., a human), diagnosed as having cancer, by administering to that mammal an amount of Gram-negative bacteria wherein the bacteria are viable, may or may not be attenuated, and have a genetic defect that results in a substantial or total loss of lipopolysaccharide within the outer membrane of the bacteria and wherein the amount administered is sufficient to inhibit the growth or metastatic potential of the cancer.

In one embodiment, the disclosure provides a method for treating a cancer comprising administering to a mammal diagnosed as having cancer an amount of viable or non-viable Gram-negative bacterial organisms that have a genetic defect that results in a substantial loss of lipopolysaccharide within the outer membrane of the bacteria, wherein the amount administered is sufficient to inhibit growth of the cancer.

In some embodiments, the genetic defect disrupts or partially disrupts the biosynthesis of KDO2-Lipid $IV_A$ or prevents the O-acylation of KDO2-Lipid $IV_A$.

In some embodiments, the cancer is a solid tumor.

In other embodiments, the mammal is further administered a chemotherapeutic agent including, for example, cyclophosphamide. In other embodiments, the mammal is further administered an antagonist of an immune function-inhibiting receptor or receptor agonist including, for example, inhibiting the function of a T-cell receptor or T-cell receptor ligand (e.g., CTLA-4, PD-1, PD-L1, and PD-L2).

In other embodiments, the mammal is further administered an agonist of an immune function-stimulating receptor including, for example, agonists that stimulate a T-cell receptor. Suitable receptor targets include, for example, GITR, 4-1BB, CD40, and OX40.

In other embodiments, the mammal is further administered an immune function-stimulating cytokine including, for example, interferon-alpha, interferon-beta, interferon-gamma, granulocyte-macrophage colony-stimulating factor, interleukin-2, and interleukin-12.

In some embodiments, the Gram-negative bacteria are *Salmonella* or *Escherichia*.

In another embodiment, the disclosure provides for methods of killing and reducing endotoxin activity and/or pyrogenicity in Gram-negative bacteria by treating the bacteria with polymyxin B and glutaraldehyde. In one embodiment, viability is reduced to 0% and the endotoxin activity or pyrogenicity is reduced by about 90% or 96%.

DETAILED DESCRIPTION

Figure 1:
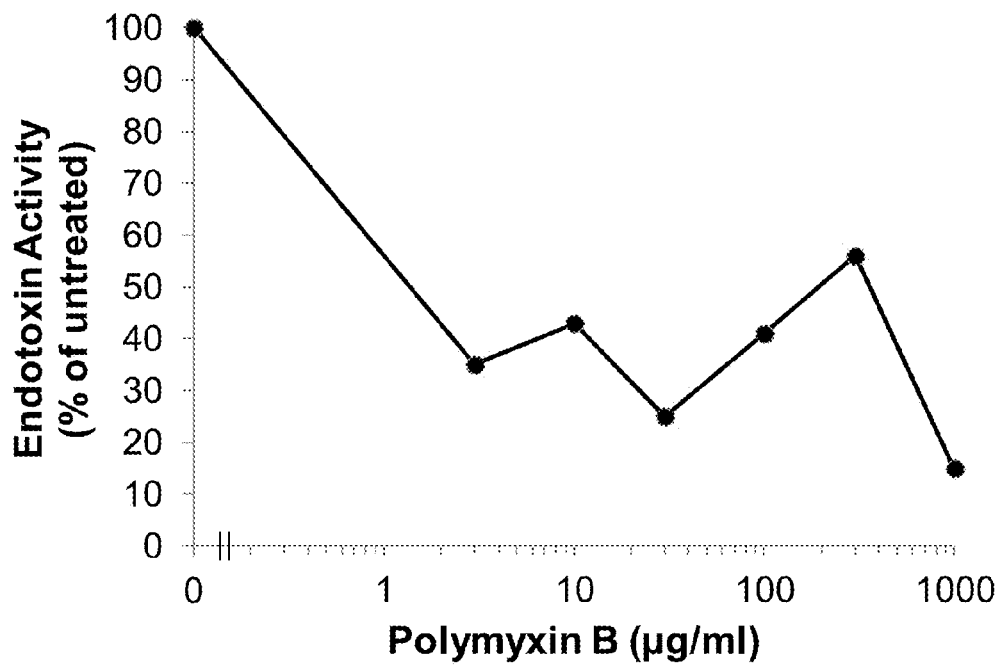
FIGS. 1 and 2 demonstrate that incubation of *E. coli* with polymyxin B (PMB) reduces the level of bacterial cell-associated endotoxin activity and cell viability. This is further described in Example 2.

Provided herein are compositions comprising non-viable Gram-negative bacterial organisms and that have substantial reduction in endotoxin and/or pyrogenic activity and methods to treat cancer, comprising administering to a mammal suffering from cancer an amount of non-viable Gram-negative bacterial organisms that have a substantial reduction in endotoxin or pyrogenic activity, wherein the amount administered is sufficient to inhibit growth or metastasis of the cancer.

Possible mechanism(s) responsible for anti-tumor activity mediated by bacteria include selective proliferation of live bacterial organisms in tumor tissue and stimulation of host immune responses, in particular via LPS (endotoxin)-mediated induction of tumoricidal cytokine release from host mononuclear cells. However, the proliferation of live bacteria and LPS (endotoxin)-mediated induction of cytokines (even with LPS attenuated by msbB mutation), are believed responsible for dose-limiting toxicity associated with treatment of mammals with live bacteria. Toso et al. (J. Clin. Oncol. 20(1):142-152, 2002) treated cancer patients with live msbB-attenuated *Salmonella* and dose-limiting toxicities included bacteremia and side-effects associated with cytokine release. Proliferation of bacteria in tumor tissue was lower and sensitivity to cytokine-mediated toxicities was higher than seen in human tumor xenograft models in mice. It is believed that systemic proliferation by viable bacteria and/or cytokine-related toxicities, mediated in part by LPS lacking one secondary acyl chain, may prevent administration of safe and effective doses of live, attenuated Gram-negative bacteria to some mammals (such as humans) other than mice, which are known to be relatively resistant to bacterial infection and associated septic consequences of cytokine induction.

Although not wishing to be bound by theory, it is believed that killed or non-viable Gram-negative organisms with substantially reduced endotoxin activity and/or pyrogenicity can be administered to cancer patients in amounts that are less toxic and more effective to treat the cancer as compared to using live or viable organisms, which proliferate in each patient's normal and tumor tissues in a variable manner that cannot be controlled by the practitioner, either proliferating insufficiently to produce a therapeutic effect or proliferating too much, thereby producing unacceptable toxicity. It is also believed that killed or non-viable Gram-negative organisms with substantially reduced endotoxin activity and/or pyrogenicity can be administered to cancer patients in amounts that are less toxic and more effective to treat the cancer as compared to using killed bacteria that express wildtype levels of endotoxin activity and/or pyrogenicity.

It is also believed that viable Gram-negative organisms having a genetic defect in the formation of LPS that results in a substantial reduction in the amount of glycosylated Lipid A and LPS in the outer membrane of the bacteria can be effective in the treatment of cancer whether administered alive and attenuated, so as to prevent further proliferation in the mammalian host, or as killed organisms. Although such organisms lack functional LPS molecules that cause endotoxic shock as well as provide a stimulus to the host's immune system, it is believed that there are other features of the Gram-negative bacteria that will stimulate the host's innate or combined innate and adaptive immune responses to achieve tumor cell killing or tumor growth inhibition.

In one embodiment, the Gram-negative organisms used in cancer therapy, as disclosed herein, do not contain DNA that encodes or expresses non-bacterial proteins (e.g., tumor-specific antigens). The Gram-negative organisms, therefore, are not a cancer vaccine in that they do not directly induce a specific immunological response against a tumor antigen. Instead, these organism function as an adjuvant or biological response modifier (BRM) that may generally stimulate the host innate immune response and possibly indirectly an adaptive anti-tumor immune response. In some embodiments, the Gram-negative organisms are injected directly in or near the site of the tumor, or are injected systemically and accumulate in or near the tumor. The increased innate immune response against the organisms then may secondarily become directed against the tumor. In addition, or alternatively, immune responses against the organisms may stimulate or activate pre-existing tumor antigen-specific immune cells capable of participating in an adaptive anti-tumor response.

In an alternative embodiment, the Gram-negative organisms express DNA that encodes for expression of non-bacterial proteins including, for example, tumor-specific antigens or immune system stimulating proteins. Here again, the organisms may be injected in or near the tumor site, or systemically, and induce an innate or adaptive immune response against the organism, the tumor-specific antigen, or both.

As used herein, the term tumor specific antigen refers to an antigen that is expressed by a tumor but is not expressed by any normal cells from the organism from which the tumor was derived. The term tumor-associated antigen refers to an antigen that is expressed by a tumor but may also be expressed in a limited manner by normal cells from the organism from which the tumor was derived. The limited manner of expression may reflect a lower level of expression in normal cells than the tumor, expression by a limited type of normal cell or expression by normal cells only during fetal development (i.e., a fetal antigen). As used herein, an antigen is any molecule that can be recognized by an immune response, either an antibody or by an immune cell (e.g., T cell).

As used herein the terms "adjuvant" and "biological response modifier" refer to any substance that enhances an immune response to an antigen, tumor or tumor-associated cell. Thus, an adjuvant or biological response modifier is used to stimulate the immune system to respond more vigorously to a foreign antigen or a disease-causing or disease-associated cell expressing a new antigen, or structurally altered or abnormal level of an existing antigen. However, in some embodiments, recombinant forms of Gram-negative bacteria that express, e.g., tumor specific or tumor-associated antigens or human immune activation proteins such as cytokines or chemokines are contemplated for use in the disclosed methods. In an alternative embodiment, purified immune activation proteins such as cytokines or chemokines are mixed with the Gram-negative organisms prior to administration, or are administered before or after the Gram-negative organisms.

As used herein the term mammal includes any mammal such as a human, dog, cat, cow, sheep, and the like. A preferred mammal is a human.

The term "Gram-negative bacteria" refers to bacteria that do not retain the initial basic dye stain (e.g., crystal violet) that is part of the procedure known as the Gram stain. In an exemplary Gram stain, cells are first fixed to a slide by heat and stained with a basic dye (e.g., crystal violet), which is taken up by both Gram-negative and Gram-positive bacteria. The slides are then treated with a mordant (e.g., Gram's iodine), which binds to basic dye (e.g. crystal violet) and traps it in the cell. The cells are then washed with acetone or alcohol, and then counterstained with a second dye of different color (e.g., safranin). Gram-positive organisms retain the initial violet stain, while Gram-negative organisms are decolorized by the wash solvent organic and hence show the counterstain. Exemplary Gram-negative bacteria include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp.

Within gram-negative organisms are the Enterobacteriaceae, a large family that includes, along with many harmless symbionts, many well-known pathogens, such as *Salmonella, E. coli, Yersinia pestis, Klebsiella* and *Shigella, Proteus, Enterobacter, Serratia*, and *Citrobacter*. Members of the Enterobacteriaceae have been referred to as enterobacteria, as several members live in the intestines of animals.

Enterobacteriaceae are rod-shaped, typically 1-5 µm in length. They are facultative anaerobes, fermenting sugars to produce lactic acid and various other end products. Most also reduce nitrate to nitrite and generally lack cytochrome C oxidase. Most have many flagella for motility, but some are nonmotile. Enterobacteriaceae are nonspore-forming.

The term "vector" refers to a nucleic acid molecule, which is capable of transporting another nucleic acid to which it is linked as a single piece of nucleic acid. Vectors capable of directing the expression of genes to which they are operatively linked are referred to herein as "expression vectors." The term "expression system" as used herein refers to a combination of components that enable sequences in an expression vector to be transcribed into RNA, folded into structural RNA, or translated into protein. The expression system may be an in vitro expression system, such as is commercially available or readily made according to known methods, or may be an in vivo expression system, such as a eukaryotic or prokaryotic host cell that contains the expression vector. In general, expression vectors useful in recombinant DNA techniques can be "plasmids" which refer generally to circular double stranded DNA that, in their vector form, is not bound to the bacterial chromosome. Other expression vectors well known in the art also can be used in expression systems (e.g., cosmid, phagemid and bacteriophage vectors).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "modulation" as used herein refers to both upregulation (i.e., activation or stimulation (e.g., by agonizing or potentiating)) and downregulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

A. Candidate Bacterial Organisms

Candidate bacterial organisms that may be employed by the methods herein are Gram-negative and are derived from those that have endotoxin activity as wildtype organisms. Exemplary Gram-negative bacteria include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp. Candidate Gram negative organisms also may be those that fall in the Enterobacteriaceae, Pseudomonadaceae, Neisseriaceae, Veillonellaceae, Bacteroidaceae, Vibrionaceae, Pasteurellaceae, and Fusobacteriaceae families. In some embodiments, the candidate organism is a species of *Salmonella* or *Escherichia* spp.

One candidate *Salmonella* organism, VNP20009, has been described by Luo et al., Oncol Res. 12(11-12):501-8, 2001. VNP20009 is a genetically modified strain of *Salmonella typhimurium* with deletions in the msbB and purI loci. Intravenous administration at doses ranging from $1 \times 10^4$ to $3 \times 10^6$ cfu/mouse of live VNP20009 to tumor bearing mice inhibited the growth of subcutaneously implanted B16F10 murine melanoma, and the human tumor xenografts Lox, DLD-1, A549, WiDr, HTB177, and MDA-MB-231. VNP20009, given intravenously also inhibited the growth of lung metastases in these animals. See also, U.S. Pat. No. 7,354,592 (Bermudes et al.).

Another candidate *Salmonella* organism is SL3235 described by Eisenstein et al. Med. Oncol. 12(2):103-8, 1995. SL3235 is an attenuated strain of *Salmonella* that when administered live can cure plasmacytoma tumor growing in mice.

Further candidate *Salmonella* include auxotrophic mutants reported by Hoffman et al., Amino Acids 37:509-521, 2009. The *S. typhimurium* A1-R mutant is auxotrophic for leu-arg and has high anti-tumor virulence. In vitro, A1-R infects tumor cells and causes nuclear destruction. A1-R administration treats metastatic human prostate and breast tumors orthotopically implanted in nude mice. A1-R administered intravenously (i.v.) to nude mice with primary osteosarcoma and lung metastasis is effective, especially against metastasis. A1-R also was reported effective against pancreatic cancer liver metastasis when administered intrasplenically to nude mice. See also U.S. Patent publication 20090300779 (Zhao et al.), and Zhao et al. (Proc. Natl. Acad. Sci. (USA) 102(3):775-760, 2005).

A variety of Gram-negative organisms suitable for the treatment of solid tumors are reported in U.S. Pat. No. 6,685,935 (Pawelek et al.). These organisms are referred to as super-infective as they replicate preferentially in the tumor after administration. Included are super-infective, tumor-specific mutants of *Salmonella* spp., e.g., *Salmonella typhimurium*. Also described are super-infective, tumor-specific mutants of *Salmonella* spp. containing a suicide gene such as thymidine kinase from Herpes simplex virus, cytosine deaminase from *E. coli*, or human microsomal p450 oxidoreductase. See also Pawelek et al., (Lancet Oncol. 4(9):548-56, 2003).

In one embodiment, *E. coli* is selected as the organism. One particular strain contemplated is *E. coli* strain 2617-143-312, (Migula) Castellani and Chalmers (ATCC® 13070™). Additional *E. coli* strains which may be used include MG1655 (ATCC® 47076) and KY8284 (ATCC® 21272).

The Gram-negative organisms used in the methods herein need not be recombinant organisms that contain or express DNA foreign to the wildtype form of the organism. However, in some embodiments, the organisms may be modified to express some non-native molecules. For example, U.S. Pat. No. 7,452,531 reports preparation and use of attenuated tumor-targeted bacteria vectors for the delivery of one or more primary effector molecule(s) to the site of a solid tumor. According to the method, effector molecules, which may be toxic when administered systemically to a host, can be delivered locally to tumors by attenuated tumor-targeted bacteria with reduced toxicity to the host. Specifically, the attenuated tumor-targeted bacteria can be a facultative aerobe or facultative anaerobe which is modified to encode one or more primary effector molecule(s). The primary effector molecule(s) include members of the TNF cytokine family, anti-angiogenic factors, and cytotoxic polypeptides or peptides. The primary effector molecules of the disclosure are useful, for example, to treat a solid tumor cancer such as a carcinoma, melanoma, lymphoma, sarcoma, or metastases derived from these tumors.

B. Reducing Bacterial Endotoxin Activity

Various methods may be used to reduce endotoxin activity and/or pyrogenicity of bacterial organisms. As used herein, the term "endotoxin activity" refers to portions of Gram-negative bacteria that can cause toxicity, including pyrogenicity and septic shock. The toxic effects attributed to endotoxin have been found to be associated with the glycosylated lipid A portion of a lipopolysaccharide molecule present in or derived from the outer membrane of Gram-negative bacteria.

The term "Lipopolysaccharide" (LPS) refers to large molecules consisting of a lipid and a polysaccharide (glycophospholipid) joined by a covalent bond. LPS comprises three parts: 1) O antigen; 2) Core oligosaccharide, and 3) Lipid A. The O-antigen is a repetitive glycan polymer attached to the core oligosaccharide, and comprises the outermost domain of the LPS molecule. Core oligosaccharide attaches directly to lipid A and commonly contains sugars such as heptose and 3-deoxy-D-mannooctulosonic acid (also known as KDO, keto-deoxyoctulosonate). Lipid A is a phosphorylated glucosamine disaccharide linked to multiple fatty acids. The fatty acids anchor the LPS into the bacterial membrane, and the rest of the LPS projects from the cell surface. Bacterial death may result if LPS is mutated or removed.

Endotoxin activity resides in the lipid A domain portion of LPS. When bacterial cells are lysed by the immune system, fragments of membrane containing lipid A are released into the circulation, causing fever (pyrogenicity), diarrhea, and a potentially fatal shock (called endotoxic or septic shock). Toxicity of LPS is expressed by lipid A through the interaction with B-cells and macrophages of the mammalian immune system, a process leading to the secretion of proinflammatory cytokines, mainly tumor necrosis factor (TNF), which may have fatal consequences for the host. Lipid A also activates human T-lymphocytes (Th-1) "in vitro" as well as murine CD4+ and CD8+ T-cells "in vivo", a property which allows the host's immune system to mount a specific, anamnestic IgG antibody response to the variable-size carbohydrate chain of LPS. On these bases, LPS has been recently recognized as a T-cell dependent antigen "in vivo".

Endotoxin activity can be measured by methods well known in the art, including, for example, the Limulus Amebocyte Lysate (LAL) assay, which utilizes blood from the horseshoe crab, can detect very low levels of LPS. The presence of endotoxin activity will result in coagulation of the limulus blood lysate due to amplification via an enzymatic cascade. Gel clotting, turbidometric, and chromogenic forms of the LAL assay are commercially available. See, e.g., Lonza, Allendale, N.J., and Clongen Labs, Germantown, Md.

Enzyme linked immunoadsorbent assay (ELISA)-based endotoxin activity assays are also known such as the EndoLISA® from Hyglos, Munich area of Germany. This assay employs an LPS specific phage protein attached to the solid phase to capture LPS, and following a wash step, the presence of LPS is determined by addition of recombinant Factor C, which when activated by LPS, cleaves a compound that then emits fluorescence. Factor C, present in the Limulus amebocyte lysate, normally exists as a zymogen, and is the primer of the coagulation cascade that occurs in the LAL test.

Endotoxin activity can also be measured by evaluating induction of TNF-alpha secretion, either from primary peripheral blood mononuclear cells in vitro, or by treating an animal with the suspected source of endotoxin and measuring TNF-alpha levels in plasma, obtained from the animal after approximately 1 to 4 hours. Primary mammalian peripheral blood mononuclear cells can be purchased from companies such as Lonza (Allendale, N.J., USA). TNF-alpha levels in cell supernatant or plasma can be determined with ELISA kits, such as those available from Thermo Scientific (Rockford, Ill., USA), Abcam (Cambridge, Mass., USA) or eBioscience (San Diego, Calif., USA).

Endotoxin activity can also be assessed in vivo by measuring pyrogenicity (rectal temperature increase) in rabbits in response to intravenously administered organisms or derivatives thereof.

The endotoxin activity and/or pyrogenicity of Gram-negative organisms may be substantially reduced as compared to that of the wildtype organism. A substantial reduction in endotoxin activity is preferably more than about 70%, more than about 75%, more than about 80%, more than about 85%, more than about 90%, more than 95% and more than about 99%.

Various methods are available to reduce the endotoxin activity of Gram-negative organisms. The methods include treatment of the organisms with an agent that binds to LPS or disrupts its formation, or by genetically manipulating the bacterial organism to modify LPS or inhibit LPS formation.

In one embodiment, reduction in endotoxin activity or pyrogenicity is achieved by treating the bacterial organisms with an antibiotic that inactivates endotoxin. A suitable such antibiotic is polymyxin B or polymyxin E. For example, Cooperstock et al., Infect Immun. 1981 July; 33(1):315-8, report that Polymyxin B treatment can reduce the inflammatory reactivity of LPS in vaccines of Gram-negative bacteria including *Bordetella pertussis*, *E. coli*, *Haemophilus influenzae*, and *Pseudomonas aeruginosa*. It is within the skill of one in the art to determine the amount of antibiotic and conditions for treatment. In one embodiment, the polymyxin, either polymyxin B or E, may be employed at a concentration of approximately 3 micrograms to 5,000 micrograms per $1\times10^7$ to $5\times10^{10}$ bacteria per milliliter. In another embodiment, the concentration of polymyxin may be from about 200 micrograms to 5,000 micrograms per $1\times10^7$ to $5\times10^{10}$ bacteria per milliliter. In one embodiment, the antibiotic is applied to the bacteria for 10 minutes to 4 hours or from about 30 minutes to about 3 hours. In one embodiment, the bacteria are grown in the presence of magnesium (Mg) in the form of $MgCl_2$ and treated with polymyxin in the presence of $MgCl_2$, as well as at a temperature suitable to maintain the bacteria's integrity. In one embodiment, the concentration of $MgCl_2$ in the growth medium is from about 0.5 mM to about 5.0 mM, or about 2 mM, and the concentration of $MgCl_2$ in the treatment medium is from about 5.0 mM to about 30 mM, or about 20 mM. In one embodiment, the temperature of the treatment medium is from about 2° C. to about 10° C., or about 4° C. Bacterial integrity is determined by efficiency of recovery in a well-defined pellet after centrifugation at 3,000×g for 10 minutes, and by electron microscopy. In a preferred embodiment, bacterial recovery after treatment and wash is greater than about 80% and the bacteria appear intact by electron microscopy.

In another embodiment, reduction in endotoxin activity is achieved by treating the bacterial organisms with an antibiotic known to disrupt the biosynthesis of KDO2-Lipid $IV_A$. For example, Goldman et al., J Bacteriol. 170(5):2185-91, 1988 describe antibacterial agents, including antibacterial agent III, which specifically inhibit CTP:CMP-3-deoxy-D-manno-octulosonate cytidylyltransferase activity and which are useful to block the incorporation of 3-deoxy-D-manno-octulosonate (KDO) into LPS of Gram-negative organisms. As LPS synthesis ceased, bacterial growth ceased. The addition of KDO to LPS precursor species lipid $IV_A$ is the major pathway of lipid A-KDO formation in both *S. typhimurium* and *E. coli*. In one embodiment, the antibiotic is antibacterial agent III and Gram-negative bacteria are treated with a suitable amount, such as, for example 5 micrograms per milliliter to 500 micrograms per milliliter for a suitable time, for example 2 to 8 hours.

A reduction in endotoxin activity may be achieved by introducing a genetic defect into the organism. The term "defect" as used herein, with regard to a gene or expression of a gene, means that the gene is different from the normal (wildtype) gene or that the expression of the gene is at a reduced level of expression compared to that of the wildtype gene. The defective gene may result from a mutation in that gene, or a mutation that regulates the expression of that gene. (e.g., transcriptional or post-transcriptional)

In one embodiment, a reduction in endotoxin activity may be achieved by introducing a genetic defect that disrupts the biosynthesis of KDO2-Lipid IV$_A$. For example, Woodard et al., U.S. Patent publication 20100272758, report viable non-toxic Gram-negative bacteria (e.g., E. coli) substantially lacking LPS within the outer membrane. The authors describe E. coli K-12 strain KPM22 as defective in synthesis of 3-deoxy-d-manno-octulosonic acid (Kdo). KPM22 has an outer membrane (OM) composed predominantly of lipid IV$_A$, an LPS precursor that lacks glycosylation. Viability of the organisms is achieved by the presence of a second-site suppressor that transports lipid IV$_A$ from the inner membrane (IM) to the outer membrane. This suppressor is reported to relieve toxic side-effects of lipid IV$_A$ accumulation in the inner membrane and provide sufficient amounts of LPS precursors to support OM biogenesis. See also, Mamat et al., (Mol Microbiol. 67(3):633-48, 2008).

In another embodiment, Bramhill et al., U.S. Patent Publication 2011-0224097, describe viable Gram-negative bacteria comprising outer membranes that substantially lack a ligand, such as Lipid A or 6-acyl lipopolysaccharide that acts as an agonist of TLR4/MD2. According to Bramhill, the bacteria may comprise reduced activity of arabinose-5-phosphate isomerases and one or more suppressor mutations, for example in a transporter thereby increasing the transporters capacity to transport Lipid IVA, or in membrane protein YhjD. One or more genes (e.g., lpxL, lpxM, pagP, lpxP, and/or eptA) may be substantially deleted and/or one or more enzymes (e.g., LpxL, LpxM, PagP, LpxP, and/or EptA) may be substantially inactive.

In another embodiment, a reduction in endotoxin activity may be achieved by introducing a genetic defect that prevents synthesis of Kdo. For example, Rick et al., (Proc Natl Acad Sci USA. 69(12):3756-60, 1972) report an auxotrophic mutant of Salmonella typhimurium that is defective in the synthesis of the 3-deoxy-D-mannooctulosonate (ketodeoxyoctonate) region of the LPS and requires D-arabinose-5-phosphate for growth. The mutant defect was due to an altered ketodeoxyoctonate-8-phosphate synthetase (kdsA) with an apparent K(m) for D-arabinose-5-phosphate 35-fold higher than that of the parental enzyme. This caused the mutant strain to be dependent on exogenous D-arabinose-5-phosphate both for growth and for synthesis of a complete LPS. In another example, Belunis et al., (J. Biol. Chem. 270(46):27646-27652, 1995) disrupted the Kdo transferase (kdtA) gene in E. coli, which prevented incorporation of Kdo into lipid IV$_A$. This mutation was lethal, but could be rescued by the conditional presence of a temperature-sensitive plasmid encoding kdtA. The development of conditional mutants in the Kdo synthesis pathway allows for growth of the bacteria, followed by transfer to the non-permissive condition, resulting in sufficient growth or survival to produce non-viable bacteria with significantly reduced endotoxin activity.

In addition to LPS-derived endotoxin, various other constituents of Gram-negative organisms can induce or contribute to pyrogenicity and septic shock, including outer membrane proteins, fimbriae, pili, lipopeptides, and lipoproteins (reviewed by Jones, M., Int. J. Pharm. Compd., 5(4):259-263, 2001). Pyrogenicity can be measured by a rabbit method, well known in the art, involving assessment of rectal temperature after intravenous administration of putative pyrogens.

It has been found that treatment of a Gram-negative organism with a combination of polymyxin B and glutaraldehyde produced a 30-fold reduction in pyrogenicity, as measured in rabbits. In one embodiment, 1,000 micrograms per milliliter (µg/mL) of polymyxin B and 1% glutaraldehyde was employed to produce a 30-fold reduction in pyrogenicity, as measured in rabbits. The pyrogenicity is reduced by a combination of polymyxin B reaction with LPS and glutaraldehyde reactivity with LPS and/or other bacterial constituents. The glutaraldehyde serves a dual role in this setting by also killing the bacteria. Thus, in one embodiment is provided a method of reducing endotoxin activity and pyrogenicity of and killing a Gram-negative bacterial microorganism by treating said bacteria with a combination of 1,000 µg/mL polymyxin B and 1% glutaraldehyde. In another embodiment, the Gram-negative bacteria are treated with a combination of polymyxin B at a dose range between about 3 µg/mL to about 1,000 µg/mL and glutaraldehyde at a dose range between about 0.1% to about 1.0%. In a further embodiment, the dose range of polymyxin B is between about 100 µg/mL to about 1,000 µg/mL and glutaraldehyde is at a dose range between about 0.5% to about 1.0%. Additionally, Gram-negative bacteria may be treated, for example with a dose range of polymyxin B between about 1,000 µg/mL to about 3,000 µg/mL and glutaraldehyde is at a dose range between about 0.5% to about 1.0%. In another aspect, Gram-negative bacteria maybe treated, for example with a dose range of polymyxin B between about 3,000 µg/mL to about 5,000 µg/mL and glutaraldehyde is at a dose range between about 0.5% to about 2.0%. In one embodiment, the endotoxin activity is reduced by about 70%, or about 75%, or about 80%, or about 85%, or about 90%, or about 92%, and pyrogenicity is reduced by about 75%, or about 80%, or about 85%, or about 90%, or about 95%, or about 97%.

C. Rendering Bacteria Non-Viable

Bacteria for administration according to the methods of the disclosure are rendered non-viable or substantially non-viable either prior to administration or become so upon administration. What is meant by "non-viable" is that the organisms are killed by treatment with an exogenous agent, and/or contain a mutation that results in an inability of the organisms to survive in a mammalian host. Substantially non-viable bacteria are strains that have had their viability reduced by at least 80%, 85%, 90%, 95%, 99%, or more. In preferred embodiments for bacteria that are not killed or not completely killed, the bacteria are further treated or modified such that they cannot proliferate within a mammalian host. In some embodiments where LPS is substantially not produced, it is contemplated that non-viable, attenuated, or viable bacteria are administered.

Preferred methods of rendering bacteria non-viable are treatment with a compound that binds to LPS, thereby blocking its endotoxin activity, or treatment with a compound that interferes with LPS biosynthesis. In both cases, LPS binding and interference with LPS synthesis, viability is reduced as a result of permeabilization of the cell envelope. Another approach is to grow bacterial strains with conditional mutations in the LPS biosynthesis pathway that are suppressed during growth and then transfer to a non-permissive condition which activates the mutation and disrupts LPS biosynthesis. In each instance, the procedure applied is one that renders the bacteria non-viable by, determining in each setting, the optimal time of treatment or dose of compound, such that viability has been substantially lost with retention of significant bacterial cell integrity. In the case where non-viability is less than 100%, bacteria can be used which contain a mutation preventing further proliferation of viable bacteria in a mammalian host (e.g. a diaminopimelic acid auxotroph, as described by Bukhari and Taylor, J. Bacteriol. 105(3):844-854, 1971 and Curtiss et al., Immunol. Invest. 18(1-4):583-596, 1989).

If alternative or additional methods of rendering bacteria non-viable are desired, a preferred method for killing bacteria is ionizing radiation (gamma rays or electron beam), but could also be done by other standard sterilization methods such as moist or dry heat, sterilant gas or vapor (see, e.g., Shintani et al., Biocontrol Science, 16(3):85-94, 2011). Additional non-standard methods of terminal sterilization that could be used include chemical treatment such as a chemical sterilant, and are summarized by Rutala and Weber (Emerg. Infect. Dis. 7(2):348-353, 2001) and Yaman (Curr. Opin. Drug Discov. Develop. 4(6):760-763, 2001). Examples of chemical gas, vapor and liquid sterilants include ethylene oxide gas (EOG), chlorine dioxide, vaporous phase of liquid hydrogen peroxide (VHP), formaldehyde, glutaraldehyde (e.g., ≥0.05% for ≥10 minutes), ortho-phthalaldehyde (OPA) (e.g. ≥0.1% for ≥5 minutes), and phenol. Methods that kill bacteria may affect the integrity of the organism. For example, the addition of heat may damage bacterial integrity, as opposed to the use of radiation. Reference to a bacterial organism as used herein includes the fully intact organism and partially degraded forms of the organism that may arise when the organisms are killed, but does not extend to subcellular fractions of the organisms that have become separated from other cellular components, such as a cell wall fraction (preparation) or a cell wall skeleton (see e.g., U.S. Pat. No. 4,436,727), cytoplasmic fraction, and the like.

D. Compositions

In one embodiment, is provided a composition comprising non-viable Gram-negative bacterial organisms having a substantial reduction in endotoxin and/or pyrogenic activity and a pharmaceutically acceptable excipient. In another embodiment, at least about 80% of the organisms are non-viable or at least about 90% of the organisms are non-viable, or about 100% of the organisms are non-viable. In one embodiment, the organisms have their viability reduced by about 80%, or by about 85%, or by about 90%, or by about 95%, or by about 100%.

In one embodiment, the endotoxin and/or pyrogenic activity is reduced by about 70%, or by about 75%, or by about 80%, or by about 85%, or by about 90%, or by about 95%. The composition may contain any contemplated amount of non-viable or viability-reduced organisms in combination with any contemplated reduction in endotoxin or pyrogenic toxicity. In another embodiment, the composition comprises at least about 100% non-viable organisms having at least about 95% reduced endotoxin activity and pyrogenicity.

Compositions described herein may be formulated in a variety of ways for use in the methods described herein. In one embodiment, the composition comprises the organisms as described throughout and a pharmaceutically acceptable carrier.

"Pharmaceutically acceptable carriers" refers to any diluents, excipients, or carriers that may be used in the compositions. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are selected with respect to the intended form of administration, that is, oral tablets, capsules, elixirs, syrups and the like, and consistent with conventional pharmaceutical practices.

The pharmaceutical compositions may be manufactured by methods well known in the art such as microbial growth in fermenters, followed by concentration and washing by centrifugation, filtration or dialysis, conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical compositions may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions are formulated for pharmaceutical administration to a mammal, preferably a human being. Such pharmaceutical compositions of the invention may be administered in a variety of ways, including parenterally. The term "parenteral" as used herein includes subcutaneous, intravenous, intramuscular, intra-articular, intra-synovial, intrasternal, intrathecal, intrahepatic, intralesional and intracranial injection or infusion techniques.

Sterile injectable forms of the compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compositions may be formulated for parenteral administration by injection such as by bolus injection or continuous infusion.

E. Methods for Treating Cancer

Cancers suitable for treatment by the methods herein include generally carcinomas, leukemias or lymphomas, and sarcomas. Carcinomas may be of the anus, biliary tract, bladder, breast, colon, rectum, lung, oropharynx, hypopharynx, esophagus, stomach, pancreas, liver, kidney, gallbladder and bile ducts, small intestine, urinary tract, female genital tract, male genital tract, endocrine glands, thyroid, and skin. Other suitable cancers include carcinoid tumors, gastrointestinal stromal tumors, head and neck tumors, unknown primary tumors, hemangiomas, melanomas, malignant mesothelioma, multiple myeloma, and tumors of the brain, nerves, eyes, and meninges.

In some embodiments, the cancers to be treated form solid tumors, such as carcinomas, sarcomas, melanomas and lymphomas.

Cancer therapy, as described herein is achieved by administering an amount of Gram-negative (live or dead as appropriate) organisms that is sufficient to inhibit growth or metastasis of the cancer. As employed herein, the phrase "a sufficient amount," refers to a dose (or series of doses) sufficient to impart a beneficial effect on the recipient thereof. The specific therapeutically effective dose level for any particular subject will depend upon a variety of factors including the type of cancer being treated, the severity of the cancer, the activity of the specific organism or combined composition, the route of administration, the rate of clearance of the organism or combined composition, the duration of treatment, the drugs (if any) used in combination with the organism, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day being generally applicable for compounds. Dosage levels for administered organisms typically fall in the range of about $10^6$ to $10^{12}$ per $m^2$. A composition can be administered parenterally, such as intravascularly, intravenously, intraarterially, intramuscularly, subcutaneously, orally or the like. Bacterial organisms can be administered parenterally, such as intravascularly, intravenously, intraarterially, intramuscularly, subcutaneously, intraperitoneally, or intravesically.

A therapeutically effective dose can be estimated by methods well known in the art. Cancer animal models such as immune-competent mice with murine tumors or immune-compromised mice (e.g. nude mice) with human tumor xenografts are well known in the art and extensively described in many references incorporated for reference herein. Such information is used in combination with safety studies in rats, dogs and/or non-human primates in order to determine safe and potentially useful initial doses in humans. Additional information for estimating dose of the organisms can come from studies in actual human cancer. For example, Toso et al. (J Clin Oncol. 20(1):142-52, 2002) report a phase I clinical trial in which live VNP20009 was administered to patients with metastatic melanoma. Patients received 30-minute intravenous bolus infusions containing 10(6) to 10(9) cfu/m(2) of VNP20009. The maximum-tolerated dose was 3×10(8) cfu/m(2). Dose-limiting toxicity was observed in patients receiving 1×10(9) cfu/m(2), which included thrombocytopenia, anemia, persistent bacteremia, hyperbilirubinemia, diarrhea, vomiting, nausea, elevated alkaline phosphatase, and hypophosphatemia.

The organisms may be administered as a pharmaceutically acceptable formulation. The term "pharmaceutically acceptable" means a material that is not biologically or otherwise undesirable, i.e., the material may be administered to an individual along with the selected organism or combined compound without causing any undesirable biological effects or interacting in a deleterious manner with any of other administered agents. This is more thoroughly described above.

The term "treating" a subject for a condition or disease, as used herein, is intended to encompass curing, as well as ameliorating at least one symptom of the condition or disease. Cancer patients are treated if the patient is cured of the cancer, the cancer goes into remission, survival is lengthened in a statistically significant fashion, time to tumor progression is increased in a statistically significant fashion, there is a reduction in lymphocytic or hematopoietic tumor burden based on standard criteria established for each type of lymphocytic or hematopoietic malignancy, or solid tumor burden has been decreased as defined by response evaluation criteria in solid tumors (RECIST 1.0 or RECIST 1.1, Therasse et al. J Natl. Cancer Inst. 92(3):205-216, 2000 and Eisenhauer et al. Eur. J. Cancer 45:228-247, 2009). As used herein, "remission" refers to absence of growing cancer cells in the patient previously having evidence of cancer. Thus, a cancer patient in remission is either cured of their cancer or the cancer is present but not readily detectable. Thus, cancer may be in remission when the tumor fails to enlarge or to metastesize. Complete remission as used herein is the absence of disease as indicated by diagnostic methods, such as imaging, such as x-ray, MRI, CT and PET, or blood or bone marrow biopsy. When a cancer patient goes into remission, this may be followed by relapse, where the cancer reappears.

The term "substantially" unless indicated otherwise means greater than about 80%, greater than about 90%, greater than about 95% and greater than about 99%.

F. Combinations for Treating Cancer

The methods of cancer therapy described herein may employ administration of Gram-negative organisms together with one or more antagonists of receptors or ligands that negatively modulate the host immune response. Antagonists may be directed to PD-1, PD-L1 or CTLA-4 and typically are administered intravenously, for example at a dose range of about 0.03 milligram per kilogram to about 30 milligram per kilogram every 1 to 4 weeks.

Programmed cell death protein 1 (PD-1) is a protein that in humans is encoded by the PDCD1 gene. PD-1 has also been designated as CD279 (cluster of differentiation 279). PD-1 is a type I membrane protein of 268 amino acids. PD-1 is a member of the extended CD28/CTLA-4 family of T cell regulators. See, e.g., Ishida et al., EMBO J. 11 (11): 3887-95, 1992. The proteins contain an extracellular IgV domain followed by a transmembrane region and an intracellular tail. The intracellular tail contains two phosphorylation sites within in an immunoreceptor tyrosine-based inhibitory motif and an immunoreceptor tyrosine-based switch motif. This suggests that PD-1 negatively regulates TCR signaling. PD-1 is expressed on the surface of activated T cells, B cells, and macrophages. PD-1 is a broad negative regulator of immune responses.

PD-1 has two ligands, PD-L1 and PD-L2, which are members of the B7 family. See, e.g., Freeman et al., J. Exp. Med. 192 (7):1027-34, 2000 and Latchman et al., Nat. Immunol. 2(3): 261-8, 2001. PD-L1 is a 40 kDa type 1 transmembrane protein that has been reported to play a major role in suppressing the immune system during pregnancy, tissue allografts, autoimmune disease and hepatitis. PD-L1 protein is upregulated on macrophages and dendritic cells (DC) in response to LPS and GM-CSF treatment, and on T cells and B cells upon TCR and B cell receptor signaling. The formation of a PD-1 receptor/PD-L1 ligand complex transmits an inhibitory signal which reduces the proliferation of CD8+ T cells (during an immune response) at the lymph nodes and PD-1 also can control the accumulation of foreign antigen specific T cells in the lymph nodes through apoptosis. PD-L2 expression is more restricted and is expressed mainly by dendritic cells and a few tumor lines.

CTLA-4 (Cytotoxic T-Lymphocyte Antigen 4), also known as CD152 (Cluster of differentiation 152), is a protein receptor that downregulates the immune system. CTLA-4 is expressed on the surface of helper, effector and immunoregulatory T-cells, which lead the cellular immune attack on antigens. The T cell can be turned on by stimulating the CD28 receptor or turned off by stimulating the CTLA-4 receptor. CTLA-4, like that of the T-cell costimulatory protein, CD28, bind to CD80 and CD86, also called B7-1 and B7-2, respectively, on antigen-presenting cells. T-cell activation through the T-cell receptor and CD28 leads to increased expression of CTLA-4, an inhibitory receptor for B7 molecules.

Enhancing or prolonging T-cell activation has been achieved by monoclonal antibodies (mAbs) to CTLA-4 and PD-1. Ipilimumab and tremelimumab are monoclonal antibodies that inhibit CTLA-4, and have been shown to induce or enhance anti-tumor immune responses leading to durable anti-tumor effects. Ipilimumab (also known as MDX-010 or MDX-101), marketed in the U.S. under the name Yervoy, is sold by Bristol Myers Squibb for the treatment of unresectable or metastatic malignant melanoma. BMS-936558 (MDX-1106) is a monoclonal antibody against PD-1 and has exhibited significant anti-tumor activity in human clinical trials. See, e.g., Brahmer et al., J. Clin. Oncol., 28(19):3167-3175, 2010, Brahmer et al., N. Engl. J. Med., 366(26):2455-2465, 2012; and Lipson et al., Clin. Can. Res. 19(2):462-468, 2013.

Inhibition of CTLA-4 also may be achieved by a fusion protein (CTLA4Ig) made up of CTLA-4 and Fc of immunoglobulin (Ig) heavy chain. See, e.g., Park et al., Pharm Res. 20(8):1239-48, 2003.

An additional important negative regulator of the immune response in the tumor microenvironment is the signal transducer and activator of transcription (STAT) signal responsive transcription factor STAT3. Activity of this factor is elevated in tumor and associated immune cells. STAT3 activity in tumor cells contributes to enhanced survival, proliferation, invasion and metastasis, as well as stimulation of angiogenesis. Elevated STAT3 activity in immune cells leads to accumulation and activation of immunosuppressive cells, such as Treg, Th17 and myeloid derived suppressor cells within the tumor microenvironment. See e.g., Rébé et al. (JAK-STAT 2(1):e23010-1-10, 2013) for review. The widely used type 2 diabetes drugs metformin and phenformin have been shown to have antitumor activity and the mechanism is thought to include inhibition of STAT3 activity, resulting in decreased anti-tumor immunosuppression. See e.g., Deng et al., (Cell Cycle 11(2):367-376, 2012), Hirsch et al., (Proc. Natl. Acad. Sci., USA 110(3):972-977, 2013), Appleyard et al., (British J Cancer 106:1117-1122, 2012), Jiralerspong et al., (J Clin Oncol. 27(20):3297-3302, 2009), and Del Barco et al., (Oncotarget 2(12):896-917, 2011) for review. The methods of cancer therapy described herein may employ administration of Gram-negative organisms together with an inhibitor of STAT3 expression or activity. Such inhibitors may include metformin and phenformin. Metformin maybe administered, for example at a dose range of between about 50 milligrams to about 1,000 milligrams, usually 1 to 3 times per day. Phenformin is typically administered at a dose range of between about 20 milligrams to about 800 milligrams 1 to 2 times per day.

The methods of cancer therapy described herein may also employ administration of Gram-negative organisms together with one or more agonists of receptors or ligands that positively modulate the host immune response. Agonists directed to 4-1BB (CD137), GITR, CD40 or OX40 (CD134) and can be administered, for example intravenously at a dose range of between about 0.03 milligram per kilogram to about 30 milligram per kilogram every 1 to 4 weeks.

Glucocorticoid inducible tumor necrosis factor receptor (TNFR)-related protein (GITR), 4-1BB (CD137), CD40 and OX40 (CD134) are costimulatory TNFR family members that are expressed on regulatory and effector T cells as well as on other cells of the immune system. Activation of these proteins leads to stimulation or enhancement of immune function. Activating monoclonal antibodies for each of these proteins have exhibited anti-tumor activity in preclinical models and have entered clinical development. See, e.g., Melero et al., Clin. Cancer Res. 15(5):1507-1509, 2009, Garber, JNCI 103(14):1079-1082, 2011, Khong et al., Int. Rev. Immunol. 31(4):246-266, 2012, Vinay and Kwon, Mol. Cancer Ther. 11(5):1062-1070, 2012, Snell et al., Immunol. Rev. 244(1):197-217, 2011, and So et al., Cytokine Growth Factor Rev. 19(3-4):253-262, 2008.

The methods of cancer therapy described herein may also employ administration of Gram-negative organisms together with one or more chemotherapeutic agents. Such agents may include cyclophosphamide. It is contemplated that when cyclophosphamide is used in the methods described herein, it may administered in a dose of between 5 mg/m$^2$ to 750 mg/m$^2$ intravenously or orally daily or every 21 days. Alternatively, cyclophosphamide may be administered, for example, in a metronomic regimen at a dose of between 5 mg to 100 mg orally daily. See, for example, Jia et al., Int. J. Cancer 121(3):666-674, 2007.

Stimulation of anti-tumor immune responses has been demonstrated with various cytokines. See, for example, Smyth et al., Immunological Rev. 202:275-293, 2004 and Kim-Schulze, Surg. Oncol. Clin N. Am. 16:793-818, 2007 for reviews. The methods of cancer therapy described herein may also employ administration of Gram-negative organisms together with recombinantly expressed or isolated and purified cytokines, such as interferon-alpha, interferon-beta, interferon-gamma, granulocyte-macrophage colony-stimulating factor, interleukin-2, and interleukin-12.

The methods of cancer therapy described herein may also employ Gram-negative bacteria administered together with recombinantly expressed or isolated and purified interferon-alpha. The interferon-alpha may be administered either subcutaneously, intramuscularly, or intravenously at a dose range of between about $3\times10^5$ to about $3\times10^8$ IU 1, 3, 5 or 7 times per week. In another embodiment, Gram-negative bacteria may be administered together with interferon-beta. In certain embodiments, the interferon-beta will be administered subcutaneously or intravenously at a dose range of between about 0.01 milligrams to about 5 milligrams either once a week or every other day. Interferon-gamma may also be co-administered. In one embodiment, the interferon-gamma may be administered either subcutaneously or intravenously at a dose range of between about $1\times10^5$ IU to about $1\times10^9$ IU either once or daily.

In additional methods, interleukins (e.g. interleukin-2, and interleukin-12) may be co-administered. In one embodiment, interleukins may be administered intravenously in a dose of between about $1\times10^4$ to about $1\times10^7$ IU once per week or up to three times a day in combination with Gram-negative bacteria. Additional methods include Gram-negative bacteria being administered, for example with Granulocyte-macrophage colony-stimulating factor either subcutaneously, intradermal, or intravenously typically at a dose range of between about 5 micrograms to about 5 milligrams, either daily or monthly. In any of the combination treatments noted throughout, it is contemplated the organisms may be administered before or after the additional cancer treatment. They may also be administered concurrently.

The following examples serve to illustrate the present disclosure. These examples are in no way intended to limit the scope of the disclosure.

EXAMPLES

Example 1

Optimal conditions for inactivation of lipopolysaccharide-associated endotoxin activity and bacterial cell killing by polymyxin B without loss of cell integrity are determined for each bacterial strain by incubating concentrated late log bacteria ($10^9$ to $10^{11}$ per mL) at 37° C. in phosphate buffered saline (PBS) with 1-100 µg/mL of polymyxin B for various times between 2 minutes and 6 hours. Viability is determined by serial dilution plating of control and treated bacterial suspensions on growth-compatible agar plates, followed by overnight incubation and colony counting. Cell integrity is determined by visual (microscope) examination and analysis of absorbance at 600 nm. Endotoxin activity is determined by the Limulus Amebocyte Lysate (LAL) assay. Soluble or excess polymyxin and cell debris, including soluble endotoxin, are removed by centrifugation-mediated washing with 0.9% NaCl (normal saline).

Alternatively, optimal conditions for isolation of intact, non-viable bacteria with defective LPS, resulting from a conditional mutation, are determined as described for polymyxin treatment, except that bacteria are grown in LB (Lysogeny broth) medium under the non-permissive condition and removed at various times, followed by analysis and processing as described for polymyxin treatment.

Polymyxin-treated bacteria or saline-washed late log phase LPS mutant/defective bacteria are freeze-dried using trehalose as the cryoprotectant (see, e.g., Leslie et al., App. Environment. Microbiol. 61(10):3592-3597, 1995; Gu et al., J. Biotech. 88:95-105, 2001 and American Type Culture Collection Bacterial Culture Guide). If desired, bacterial viability is further reduced by treatment with ionizing radiation at a dose sufficient to reduce viability to 0%, without loss of bacterial integrity.

Freeze-dried bacteria are resuspended in sterile water prior to use in anti-tumor studies. PBS-washed murine tumor cells (B16 and B16F10 melanoma, CT-26 colorectal carcinoma, Panc02 pancreatic carcinoma or Lewis Lung carcinoma ($10^5$-$10^7$ cells, depending on cell line) are implanted subcutaneously on the back of shaved C57BL/6 mice. Mice are randomized and treatment is initiated when tumors can be first palpated, when tumors have reached an average volume of 75 mm$^3$, or when tumors have reached an average volume of 300 mm$^3$ (as estimated by caliper measurement). Resuspended bacteria are injected once to twice per week via the tail vein or intraperitoneally (i.p.) at individual doses ranging from $10^3$ to $10^{10}$ per 0.1-0.2 mL injection volume. Antibody antagonists or agonists directed to T-cell receptors are administered i.p. at individual doses of 3-100 micrograms once to twice per week. Cyclophosphamide is administered i.p. at up to 150 mg/kg every other day for 5 days (MTD dosing) or at 25 mg/kg per day in the drinking water (metronomic dosing). Mice are weighed twice per week and clinical observations are recorded. Tumor measurements (by caliper) are carried out twice per week and mice are humanely sacrificed if/when tumors reach 1,000 mm$^3$, become necrotic or if ≥15% weight loss is observed. Tumors are removed and weighed, and minimal necropsy is carried out with sacrificed mice. Mice may be re-challenged with tumor cell implantation if long-term tumor regression or cures are observed.

Example 2

In Example 2, *E. coli* strain 2617-143-312 (Migula) Castellani and Chalmers (ATCC® 13070™) were used. This non-hazardous Gram-negative bacterium requires exogenous diaminopimelic acid (DAP) for growth. Since mammals do not make DAP, this bacterial strain is not viable and cannot cause infections in mammals. In addition, the DAP auxotrophy can be used to monitor contamination during in vitro studies. Bacteria were grown to late log phase (based on O.D.$_{600}$) in LB Miller broth with 2 mM $MgCl_2$, 0.5% glucose and 1 mM DAP at 37° C. with constant shaking at 300 rpm. The culture was washed three times by centrifugation at 2,000×g for 15 minutes and resuspension in 4° C. LB Miller broth containing 20 mM $MgCl_2$, 0.5% glucose and 0.1 mM DAP (PMB treatment medium). Final resuspension was made at $2\times10^{10}$ bacteria per mL, based on an O.D.$_{600}$ of 1 being equal to $1.12\times10^9$ bacteria per mL. Individual aliquots of the culture were incubated without and with various concentrations of Polymyxin B (PMB) (Calbiochem #5291) for 1 hour at 4° C. with constant stirring. Bacteria were then washed three times with 4° C. fresh PMB treatment medium by centrifugation at 3,000×g for 10 minutes and resuspended at $2\times10^9$ bacteria per mL. Bacteria recovery efficiency was monitored by following O.D.$_{600}$. Bacteria recovery after PMB treatment and wash was greater than 90% for all samples treated with up to 300 µg/mL PMB, and exceeded 80% for treatment with 1,000 µg/mL PMB.

In FIG. 1, endotoxin activity was determined by analyzing serial dilutions of untreated and treated bacterial cultures with the Limulus Amebocyte Lysate (LAL) Endosafe Endochrome-K kinetic assay kit (Charles River Endosafe, Charleston, S.C.). Untreated cultures typically contained approximately 50-100 endotoxin units per $1\times10^6$ bacteria.

Similar endotoxin reductions were observed for treatment with 1,000 µg/mL PMB in four independent experiments (average=17% of untreated).

Figure 2:
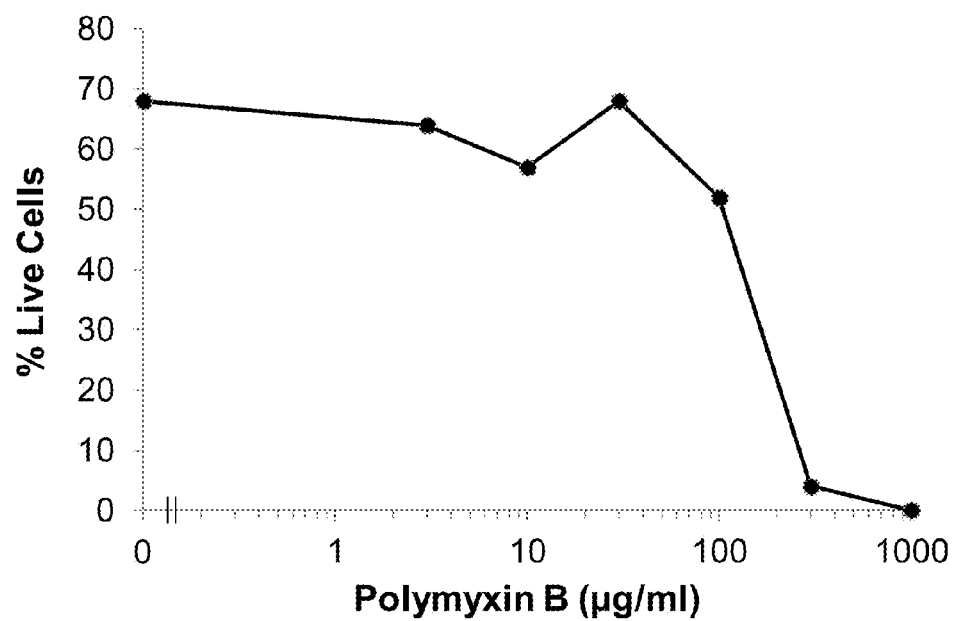

In FIG. 2, bacterial viability was determined by serially diluting and plating each sample on LB Miller agar plates containing 2 mM $MgCl_2$, 0.5% glucose, with and without 1 mM DAP (to monitor viability and contamination, respectively). Plates were incubated overnight at 37° C., the number of colonies on each plate was determined, and then viability was calculated by multiplying the number of colonies on each plate by the dilution factor. The total number of bacteria in each suspension was calculated by multiplying the $O.D._{600}$ by the conversion factor of $1.12 \times 10^9$ bacteria/mL per $O.D._{600}$ of 1. Viability (% Live Bacteria) was calculated as the percent of viable bacteria/mL relative to the total number of bacteria. Treatment with 1,000 µg/mL PMB reduced bacteria viability to 0%. In subsequent scale-up experiments 1,000 µg PMB reduced viability to an average of 11% in four independent experiments.

Example 3

Figure 3:
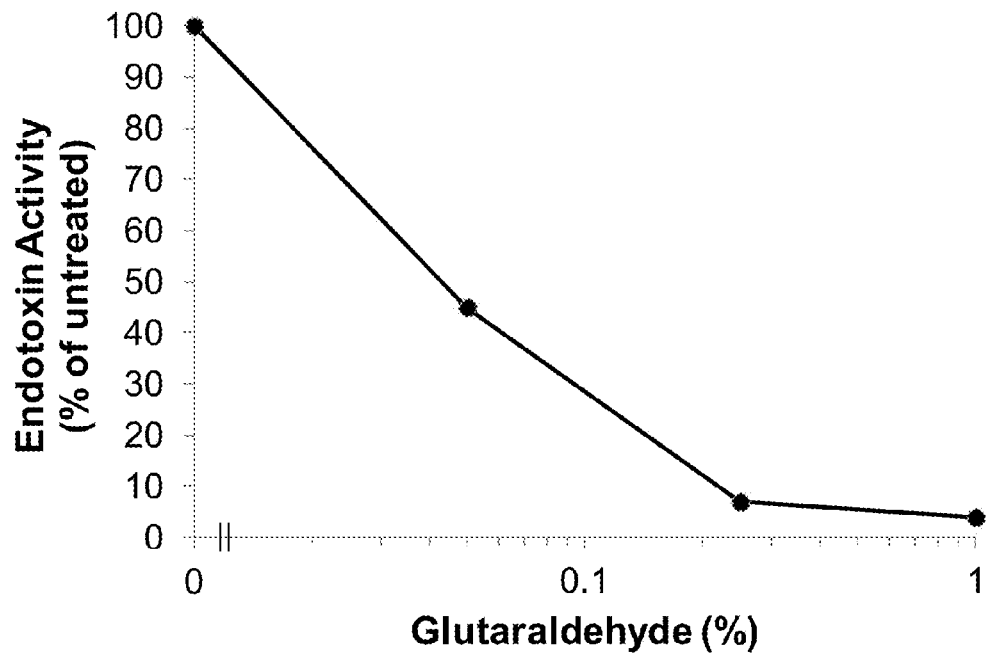
FIGS. 3 and 4 demonstrate that incubation of *E. coli* with glutaraldehyde (GA) reduces the level of bacterial cell-associated endotoxin activity and cell viability, as further described in Example 3.

The experiments were carried out as described in Example 2, except that pre-treatment washes, glutaraldehyde (GA) treatment and post-treatment washes were carried out with phosphate-buffered saline (PBS; Mg and Ca-free) pH 7.5, containing 20 mM $MgCl_2$. Bacteria recovery after GA treatment, at all concentrations tested, was typically 80-100%. FIG. 3 demonstrates that treatment with 1% GA reduced endotoxin activity by 96%. A 2-liter scale-up experiment with 1% GA treatment produced an endotoxin activity reduction of 82%, relative to the untreated culture.

Figure 4:
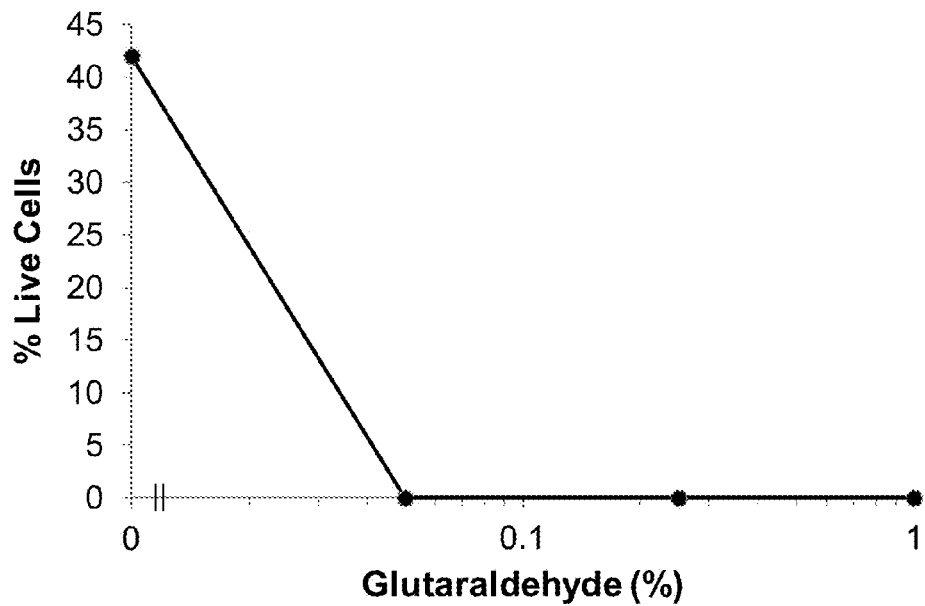

Treatment with GA consistently produced 100% bacteria kill at doses above 0.05%, as demonstrated in FIG. 4.

Combination of 1,000 µg/mL PMB treatment followed by 1% GA treatment using 2 liters of late log phase culture produced bacteria with 0% viability and a 92% (12-fold) reduction in endotoxin activity, relative to the untreated culture (Table 1).

Example 4

Figure 5:
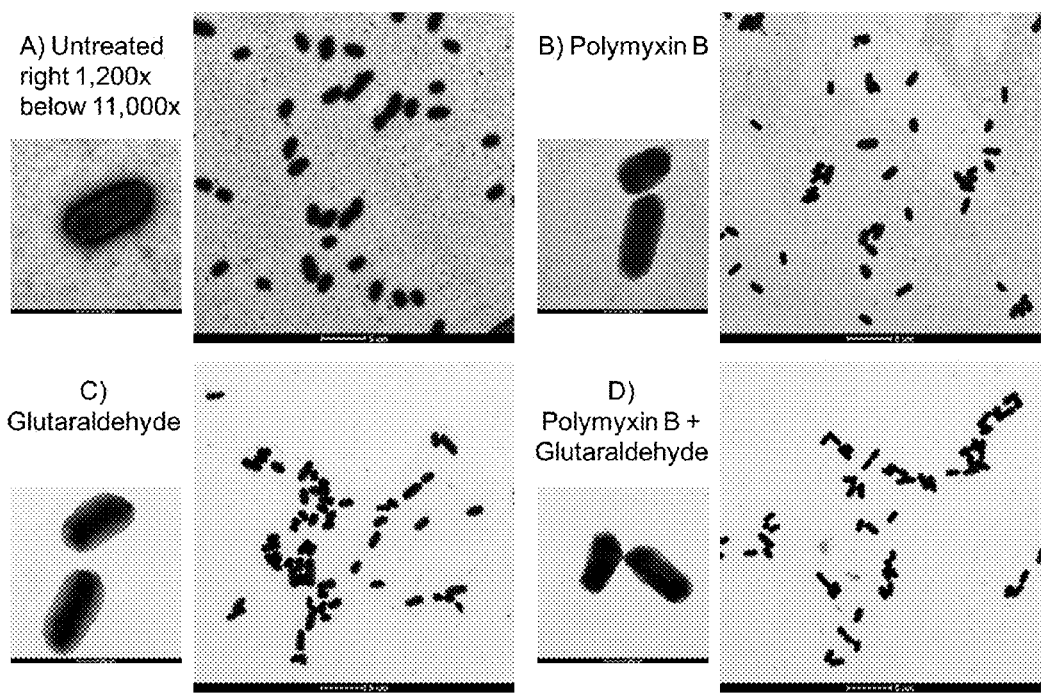
FIG. 5 depicts transmission electron microscope images of *E. coli* untreated (FIG. 5A), treated with 1,000 µg/mL PMB (FIG. 5B), 1% GA (FIG. 5C), or both PMB and GA (FIG. 5D), demonstrating that the bacteria remain intact after all treatments, as further described in Example 4.

In Example 4, bacteria were grown and treated with 1,000 µg/mL PMB, 1% GA or both as described in the protocols for Examples 2 and 3. Samples were diluted with PBS, pH 7.5 containing 1% GA (if not previously exposed to GA) and fixed for 10 minutes. Twenty-five microliter droplets containing the bacteria were placed on parafilm and then covered with a 100 mesh formvar+carbon EM grid (EMS, Hatfield, Pa.), which was pre-coated with 0.1% poly-L-lysine. Samples were allowed to adhere for 10 minutes and then the grids were washed briefly three times by placement on 200 microliter water droplets. The grids were negatively stained by placement for 1 minute on 100 microliter droplets of 2% uranyl acetate in water. Excess stain was blotted away with 3M filter paper, followed by air drying. Samples were visualized using an FEI Tecnai Spirit G2 BioTWIN transmission electron microscope equipped with a bottom mount Eagle 4 k (16 megapixel) digital camera (magnifications 1,200× and 11,000×). The images in FIGS. 5B, 5C, and 5D confirm that PMB and/or GA treatments carried out according to the present methods leave the bacteria intact, which is a desirable result. A polysaccharide capsule is visible (fuzzy surface) on the untreated bacteria (FIG. 5A), but appears to have been removed or matted down in all treated bacteria (FIGS. 5B, 5C, and 5D).

Example 5

For Example 5, E. coli were grown and treated with 1,000 µg/mL PMB plus 1% GA, and viability and endotoxin levels were determined as described for Examples 2 and 3. After final washing, untreated and PMB+GA-treated bacteria were resuspended in 50% PBS, pH 7.5, 0.5 mM $MgCl_2$, 12% trehalose at a concentration of $1.1 \times 10^{11}$ bacteria per mL, aliquoted, flash frozen and stored at −80° C. The pyrogenicity threshold was determined essentially as described in the *United States Pharmacopeia*, Chapter 151. Adult female New Zealand White rabbits weighing at least 2.0 kg were used. All animals were conditioned with a sham test not more than 7 days prior to the pyrogen test. Dose range-finding was carried out with one rabbit per dose and these results were subsequently confirmed with two rabbits per dose. Bacteria were diluted into sterile saline for injection. All doses were delivered via the intravenous route in a volume of 10 mL. The lowest concentration of test agent that produced a temperature increase of 0.5-1.0° C. at any time point within three hours of test agent administration was considered to represent the pyrogenicity threshold. Rectal temperatures were recorded at baseline and at 30 minute intervals between 1 and 3 hours following injection of test agent. Saline-diluted vehicle used for storage of untreated and treated E. coli was shown not to be pyrogenic. Administration of $3 \times 10^4$ untreated bacteria to two rabbits produced temperature increases of 0.8 and 1.0° C. Administration of $3 \times 10^5$ PMB+GA-treated bacteria did not produce a temperature increase of more than 0.1° C., but administration of $9 \times 10^5$ PMB+GA-treated bacteria to two rabbits produced temperature increases of 0.7 and 1.0° C., demonstrating a pyrogenicity threshold difference of 30x-fold. It is likely that PMB neutralizes only lipopolysaccharide-mediated pyrogenic activity. Whereas, GA may neutralize pyrogenicity mediated by lipopolysaccharide, as well as by other constituents of the bacteria.

Table 1 demonstrates the pyrogenicity (febrile reaction) threshold for untreated bacteria and bacteria treated with both 1,000 µg/mL PMB and 1% GA, as measured by a standard in vivo rabbit test. The results are compared to endotoxin levels determined with the in vitro LAL assay, demonstrating that although PMB+GA treatment reduces endotoxin levels by 12-fold, pyrogenicity mediated by the same sample is reduced by 30-fold, compared to untreated bacteria.

TABLE 1

| Treatment | Live Bacteria | Endotoxin Activity LAL Assay | Pyrogenicity Threshold Rabbit Assay |
| --- | --- | --- | --- |
| No Treatment | 83% | 44.7 Units/$10^6$ Bacteria | $3 \times 10^4$ Bacteria |
| PMB + GA | 0% | 3.6 Units/$10^6$ Bacteria | $9 \times 10^5$ Bacteria |
| Max Reduction | | 12X | 30X |

Example 6

In Example 6, E. coli were grown and treated with 1,000 µg/mL Polymyxin B plus 1% GA as described in the protocols for Examples 2 and 3. Frozen stocks of untreated and treated bacteria were thawed rapidly at 37° C. and either diluted at least 10-fold into sterile saline for injection (i.v. doses $\leq 3 \times 10^9$ bacteria) or centrifuged at 3,000×g for 10 minutes and resuspended in sterile saline for injection (i.v.

doses ≥5×10$^9$). Bacteria or vehicles were injected i.v. via the tail vein in a volume of 100 microliters.

Eight week old C57BL/6 or BALB/c female mice were used and acclimated for at least 7 days prior to studies. Mortality and clinical observations were performed once or twice per day. Additional observations were made at the time of and 1-4 hours after injections. Lack of toxicity by vehicles was confirmed. Cage side observations included but were not limited to the following:

Changes in skin, fur, eyes, mucous membranes, gait, posture, and response to handling occurrence of secretions/excretions or other evidence of autonomic activity such as lacrimation, piloerection, unusual respiratory patterns; presence of seizures; changes in general alertness; stereotype behaviors such as excessive grooming and repetitive circling; unusual behaviors (self-mutilating); development of lumps/bumps (tumor, abscess, etc.); development of signs of stress and/or respiratory symptoms; observation of the injection sites for signs of irritation and inflammation; changes in food and water consumption and urine and feces output.

Bacteria administration for multiple-dose studies was carried out twice per week for two weeks (4 treatments). Evaluation of toxicity included monitoring of animal weight. The mice used in the multiple-dose study reported for PMB+GA-treated bacteria at 1×10$^9$ were tumor-bearing. All other mice reported in Table 2 were non-tumor bearing.

TABLE 2

| Bacterial Treatment | Dose | Single Dose Observations | Multiple (4) Dose Observations |
|---|---|---|---|
| Untreated | 3 × 10$^8$ | Slightly lethargic at 1-4 hr | Slightly lethargic at 1-4 hr |
|  | 1 × 10$^9$ | Lethargic at 1-4 hr | Lethargic at 1-4 hr, 2 of 3 mice dead after 4$^{th}$ dose |
|  | 5 × 10$^9$ | Lethargic at 1-48 hr Dead by 72 hr | ND* |
|  | 1 × 10$^{10}$ | Dead by 18 hr | ND |
| PMB + GA | 1 × 10$^9$ | Slightly lethargic at 1-4 hr | Slightly lethargic at 1-4 hr, ruffled fur |
|  | 3 × 10$^9$ | Lethargic at 1-4 hr | Slightly lethargic, lethargic or ruffled fur up to 4 hr post treatment |
|  | 5 × 10$^9$ | Lethargic at 1-4 hr | Slightly lethargic, lethargic or ruffled fur up to 4 hr post treatment |
|  | 1 × 10$^{10}$ | Severely lethargic, 1 of 3 mice dead by 24 hr | Lethargic, slightly lethargic, ruffled fur and/or shallow breathing |

*ND = not determined

Example 7

Figure 6:
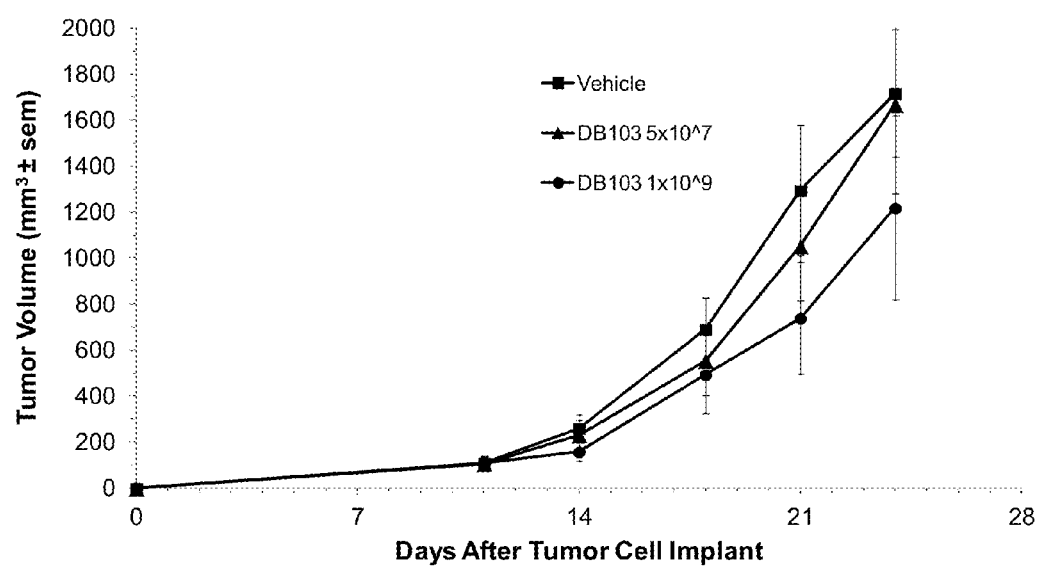
FIG. 6 depicts a graph showing the dose-dependent effect of PMB+GA-treated *E. coli* on the growth of subcutaneous murine B16F10 melanoma in mice, as further described in Example 7.
Figure 7:
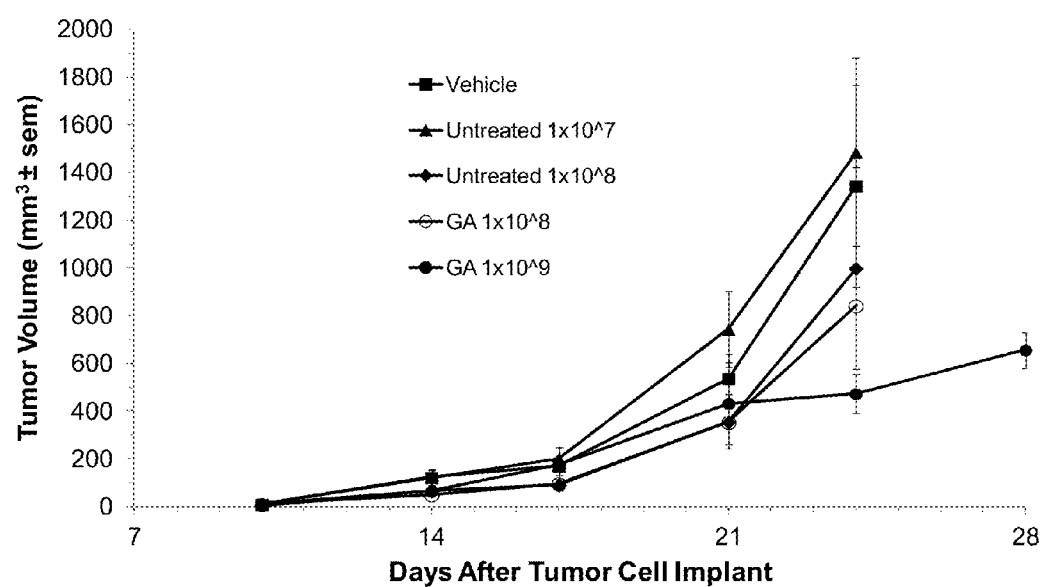
FIG. 7 shows a graph showing the dose-dependent effect of untreated and 1% GA-treated *E. coli* on the growth of subcutaneous murine B16F10 melanoma in mice, as further described in Example 8.

In Example 7, 1,000 μg/mL PMB+1% GA-treated bacteria (DB103) were prepared as described in the protocols for Examples 2 and 3. Eight week old female C57BL/6J mice were shaved at the injection site and injected subcutaneously on the right flank with 2×10$^5$ B16F10 murine melanoma cells (ATCC CRL-6475). Treatments were started via tail vein i.v. administration three days later and continued twice per week for a total of 5 treatments. DB103 in 50% PBS, pH 7.5, 0.5 mM MgCl$^2$, 12% trehalose at a concentration of 1.1×10$^{11}$ per mL were diluted 11-fold (1×10$^9$ dose) or 220-fold (5×10$^7$ dose) with sterile saline and injected in a final volume of 100 microliters. The stock vehicle was diluted 11-fold for the vehicle control treatment group. Tumors were measured with calipers twice weekly and tumor volume was determined using the formula (length×width$^2$)/2. No compound-related deaths were observed. All animals developed tumors, with the exception of two animals treated with 1×10$^9$ DB103. Transient body weight loss of up to 3% (low dose group) and 7% (high dose group) was observed, but recovered after the last treatment (FIG. 6).

Example 8

For Example 8, E. coli (untreated and 1% GA-treated) were prepared as described in the protocols for Examples 2 and 3. The experiment was carried out as described in the protocol for Example 7, except that treatment was started on day 11 when tumors were just palpable. Group measurements were not recorded after day 24 for most groups because a subset of animals in each of these groups had to be euthanized due to tumor burden. Tumors formed in all animals. Maximum weight loss in the 1×10$^9$ GA group was 11%. Toxicity precluded administration of 1×10$^9$ untreated E. coli (see Table 2).

Example 9

Figure 8A:
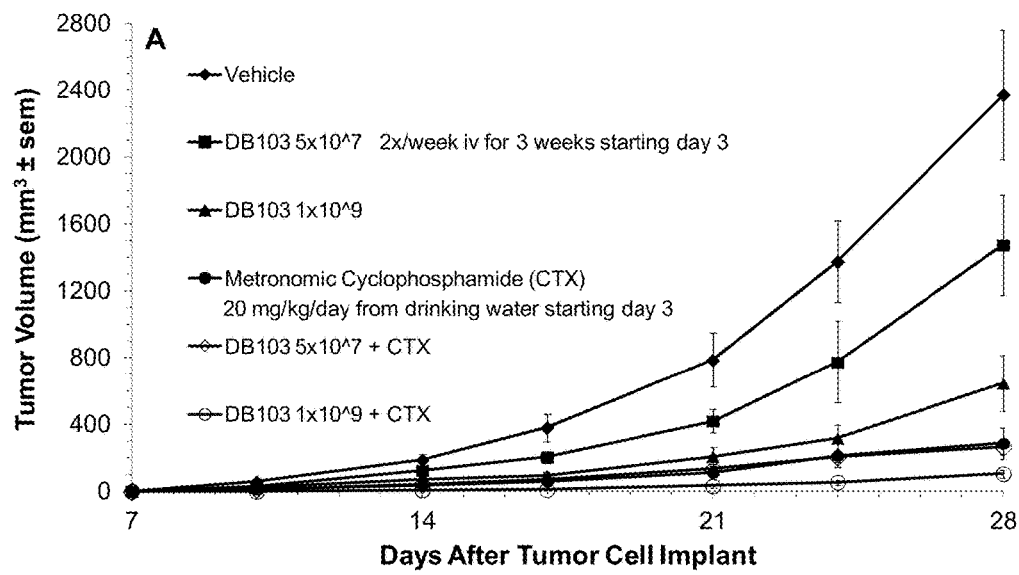
FIGS. 8A and 8B illustrate graphs showing the dose-dependent effect of PMB+GA-treated *E. coli* without and with metronomic cyclophosphamide (FIG. 8A) or anti-murine CTLA-4 antibody (FIG. 8B) on the growth of subcutaneous CT26 murine colorectal carcinoma in mice, as further described in Example 9.
Figure 8B:
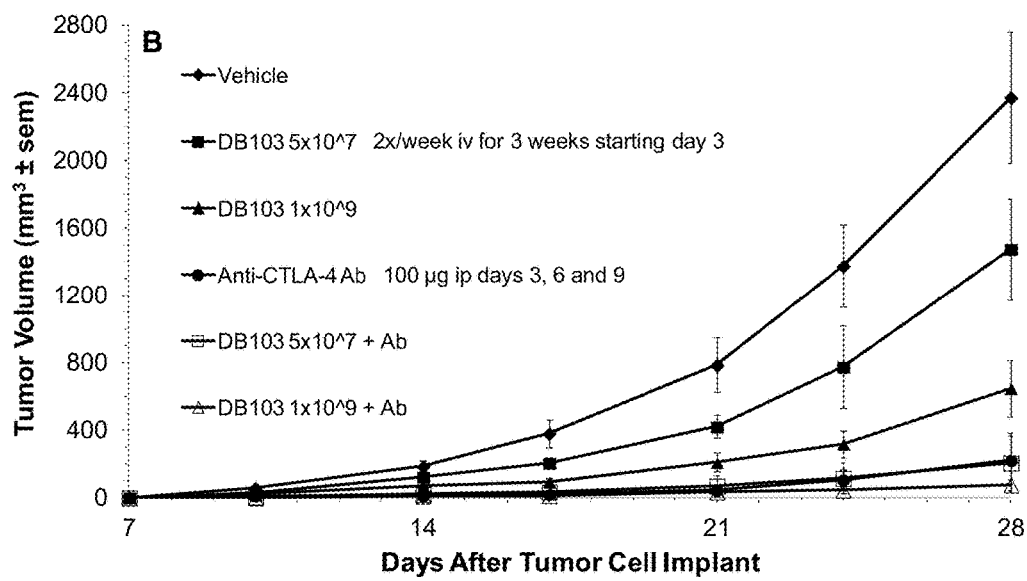

In Example 9, 1,000 μg PMB+1% GA-treated bacteria (DB103) were prepared as described in the protocols for Examples 2 and 3. The experiment was carried out as described in the protocol for Example 7, except that 1×10$^5$ murine CT26 colorectal carcinoma cells were injected subcutaneously in the right flank of BALB/c mice. DB103 treatments were started via tail vein i.v. administration three days later and continued twice per week for a total of 6 treatments. Cyclophosphamide (LKT Laboratories, #C9606) was administered via the drinking water continuously, starting on day 3, at ~20 mg/kg/day (0.133 mg/mL in water). Anti-murine CTLA-4 antibody (BioXcell #BE0164), 100 μg in 200 microliters PBS, was administered i.p. on days 3, 6 and 9. Clinical observations and mortality were recorded daily. Tumors were measured with calipers twice weekly and tumor volume was determined with the formula (length×width$^2$)/2. Tumors formed in all mice in the vehicle group. No weight loss and no compound-related deaths were observed in any group. The data for the vehicle, low dose and high dose DB103 groups is the same in FIGS. 8A and 8B.

All patents and publications mentioned in the specification are indicative of the levels of those of ordinary skill in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present disclosure has been specifically described by preferred embodiments and optional features, modification and variation of the concepts herein disclosed may be resorted to by those skilled in the art, and that such modifications and variations are considered to be within the scope of this disclosure as defined by the appended claims. Other embodiments are set forth within the following claims.

What is claimed:

1. A method of treating a cancer in a mammalian cancer patient comprising administering to the patient an amount of intact and substantially non-viable Gram-negative bacterial cells that are treated with polymyxin B or polymyxin E and glutaraldehyde under conditions to maintain the integrity of the Gram-negative bacterial cells, to reduce the viability and pyrogenicity of the Gram-negative bacterial cells, wherein the Gram-negative bacterial cells so treated have at least 80% reduction in pyrogenicity compared to corresponding wild-type Gram-negative bacterial cells and wherein the amount administered is sufficient to inhibit growth or metastasis of the cancer.

2. The method of claim 1, wherein the cancer is a solid tumor.

3. The method of claim 1, wherein the mammalian cancer patient is further administered an antagonist of an immune function inhibiting T-cell receptor or T-cell receptor ligand selected from the group consisting of CTLA-4, PD-1, PD-L1 and PD-L2.

4. The method of claim 1, wherein the mammalian cancer patient is further administered an agonist of an immune function stimulating T-cell receptor selected from the group consisting of GITR, 4-1BB, CD40 and OX40.

5. The method of claim 1, wherein the mammal is further administered a chemotherapeutic agent.

6. The method of claim 5, wherein the chemotherapeutic agent is cyclophosphamide.

7. The method of claim 1, wherein the mammal is further administered a cytokine.

8. The method of claim 1, wherein the Gram-negative bacterial cells are *Salmonella* cells.

9. The method of claim 1, wherein the Gram-negative bacterial cells are *Escherichia* cells.

10. The method of claim 1, wherein the reduction of the pyrogenicity is as measured by in vitro Limulus amebocyte lysate (LAL) assay.

11. The method of claim 1, wherein the reduction of the pyrogenicity is as measured by in vivo rabbit test.

12. The method of claim 1, wherein 100% of the Gram-negative bacterial cells are non-viable.

* * * * *